United States Patent
Jonker et al.

(10) Patent No.: US 8,906,854 B2
(45) Date of Patent: Dec. 9, 2014

(54) METHODS FOR TREATING METABOLIC DISORDERS USING FGF

(71) Applicant: Salk Institute for Biological Studies, La Jolla, CA (US)

(72) Inventors: Johan W. Jonker, Gronigen (NL); Michael Downes, San Diego, CA (US); Ronald M. Evans, La Jolla, CA (US); Jae Myoung Suh, San Diego, CA (US)

(73) Assignee: Salk Institute for Biological Studies, La Jolla, CA (US)

(*) Notice: Subject to any disclaimer, the term of this patent is extended or adjusted under 35 U.S.C. 154(b) by 0 days.

(21) Appl. No.: 14/184,621

(22) Filed: Feb. 19, 2014

(65) Prior Publication Data

US 2014/0171361 A1 Jun. 19, 2014

Related U.S. Application Data

(62) Division of application No. 13/641,451, filed as application No. PCT/US2011/032848 on Apr. 18, 2011, now abandoned.

(60) Provisional application No. 61/325,253, filed on Apr. 16, 2010, provisional application No. 61/325,255, filed on Apr. 16, 2010, provisional application No. 61/325,261, filed on Apr. 16, 2010.

(51) Int. Cl.
*A61K 38/18* (2006.01)
*A61K 9/00* (2006.01)
*A61K 45/06* (2006.01)

(52) U.S. Cl.
CPC ........... *A61K 38/1825* (2013.01); *A61K 9/0019* (2013.01); *A61K 45/06* (2013.01)
USPC ........................................................ 514/9.1

(58) Field of Classification Search
CPC A61K 38/1825; A61K 45/06; A61K 2300/00
See application file for complete search history.

(56) References Cited

U.S. PATENT DOCUMENTS 5,885,960 A * 3/1999 Nies ................................ 514/9.1
6,982,170 B1 1/2006 Maciag et al.
7,700,558 B2 * 4/2010 Thomason et al. ............ 514/6.9
8,053,408 B2 * 11/2011 Thomason et al. ............ 514/9.1
2008/0260703 A1 * 10/2008 Riordan et al. ............... 424/93.7

FOREIGN PATENT DOCUMENTS

WO WO 2004/003179 A1 1/2004
WO WO 2004/108167 A1 12/2004
WO WO 2005/063807 A2 7/2005

OTHER PUBLICATIONS

Beenken et al.; "The FGF family: biology, pathophysiology and therapy"; *Nat. Rev.*; 8:235-253 (2009).
Hutley et al.; "Fibroblast Growth Factor 1"; *Diabetes*; 53:3097-3106 (Dec. 2004).
Ikezono et al.; "The effect of satiation of the acidic fibroblast growth factor-like activity on ingestion of soyamalt and soybean milk"; *Int. J. Obesity*; 25(S2):S142 (May 2001) Abstract P403.
Inchovska et al.; "Role of FGF1, FGF2, FGF7 in the development of pancreas from control and streptozotocin-treated hamsters"; *Cell Proliferation*; 39:537550 (2006).
Inchovska et al.; "Fibroblast growth factors promote pancreatic cell proliferation in normal and STZ-treated hamsters"; *Arch. Med. Sci.*; 2:90-93 (2006).
Inchovska et al.; "Role of FGF1, FGF2 and FGF7 in the Development of the Pancreas of Diabetic Hamsters"; *Acta morphologica et anthropologica*; 12:79-85 (2007).
Jonker et al.; "A PAPRγ-FGF1 axis is required for adaptive adipose remodelling and metabolic homeostasis"; *Nature*; 485(7398):391-394 (2012).
Kilkenny et al.; "Fibroblast growth factor receptor-1 signaling in pancreatic islet beta-cells is modulated by the extracellular matrix"; *Molecular Endocrinology*; 22(1):196-205 (2008).
Ogneva et al.; "The effect of in vitro fibroblast growth factors on cell proliferation in pancreas from normal and streptozoticin-treated rats"; *Diabetes Res. Clin. Practice*; 57(1):11-16 (2002).
Widberg et al.; "Fibroblast growth factor receptor 1 is a key regulator of early adipogenic events in human preadipocytes"; *Am. J. Physiol. Endocrinol. Metab.*; 296:E121-E131 (2009).

* cited by examiner

*Primary Examiner* — Marianne P Allen
(74) *Attorney, Agent, or Firm* — Klarquist Sparkman, LLP

(57) ABSTRACT

The method provides methods and compositions for treating metabolic disorders such as impaired glucose tolerance, elevated blood glucose, insulin resistance, dyslipidaemia, obesity, and fatty liver.

40 Claims, 28 Drawing Sheets

SEQUENCE LISTING

<160> NUMBER OF SEQ ID NOS: 17

<210> SEQ ID NO 1
<211> LENGTH: 88
<212> TYPE: DNA
<213> ORGANISM: Bos primigenius

<400> SEQUENCE: 1
ataactgtcc tttcacctgg cagctgtcca gccctcaaat agctcttgtg tttggtccaa    60
aaataagatc acatgagaag gggagaaa    88

<210> SEQ ID NO 2
<211> LENGTH: 87
<212> TYPE: DNA
<213> ORGANISM: Canis lupus familiaris

<400> SEQUENCE: 2
acaccggtcc tttcgcctgg cagctgtcca gccccaaat agcttttgtg tccattccaa    60
aaataagatc acatgagagg ggagaaa    87

<210> SEQ ID NO 3
<211> LENGTH: 88
<212> TYPE: DNA
<213> ORGANISM: Equus ferus caballus

<400> SEQUENCE: 3
agaactgccc tttcacctgg cagctctcca gcccgcaaat agcttttgtg tccagtccaa    60
aaataagatc acatgaaagg gggagaaa    88

<210> SEQ ID NO 4
<211> LENGTH: 88
<212> TYPE: DNA
<213> ORGANISM: Pan troglodytes

<400> SEQUENCE: 4
atcattgtcc tttcacctgg cagctgtcca gccccaaat agcttttgtg tccagtccaa    60
aaataagatc acatgagagg gggagaaa    88

<210> SEQ ID NO 5
<211> LENGTH: 88
<212> TYPE: DNA
<213> ORGANISM: Homo sapiens

<400> SEQUENCE: 5
atcactgtcc tttcacctgg cagctgtcca gccccaaat agcttttgtg tccagtccaa    60
aaataagatc acatgagagg gggagaaa    88

<210> SEQ ID NO 6
<211> LENGTH: 88
<212> TYPE: DNA
<213> ORGANISM: Pongo pygmaeus

<400> SEQUENCE: 6
atcattgtcc tttcacctgg cagctgtcca gccccaaat agcttttgtg tccagtccaa    60
aaataagatc acatgagagg gggagaaa    88

<210> SEQ ID NO 7
<211> LENGTH: 84
<212> TYPE: DNA
<213> ORGANISM: Rattus norvegicus

<400> SEQUENCE: 7
atatttagcc tttcacctgg cagctatcca gcccccaaat agcctgcgtg tctaatccaa    60
aaataaatca catgagagga aaaa    84

<210> SEQ ID NO 8
<211> LENGTH: 84
<212> TYPE: DNA
<213> ORGANISM: Mus musculus

<400> SEQUENCE: 8
atatttgtcc tttcacctgg cagctgtcca gcccccaaat agcctgcgtg tctaatccaa    60
aaataaatca cacgagaggg gaaa    84

<210> SEQ ID NO 9
<211> LENGTH: 86
<212> TYPE: DNA
<213> ORGANISM: Didelphis virginiana

<400> SEQUENCE: 9
atgtttgtcc ttttatctgg ctgatttcca gcccccaaat agctcttatg tctactccaa    60
aaataagatc acatgaaggg gaaaaa    86

<210> SEQ ID NO 10
<211> LENGTH: 13
<212> TYPE: DNA
<213> ORGANISM: Artificial sequence
<220> FEATURE:
<223> OTHER INFORMATION: Synthetic polynucleotide

<400> SEQUENCE: 10
aggtcaaagg tca    13

<210> SEQ ID NO 11
<211> LENGTH: 13
<212> TYPE: DNA
<213> ORGANISM: Homo sapiens

<400> SEQUENCE: 11
aggtgaaagg aca    13

<210> SEQ ID NO 12
<211> LENGTH: 13
<212> TYPE: DNA
<213> ORGANISM: Mus musculus

<400> SEQUENCE: 12
aggtgaaagg aca    13

<210> SEQ ID NO 13
<211> LENGTH: 13
<212> TYPE: DNA
<213> ORGANISM: Rattus norvegicus

<400> SEQUENCE: 13
aggtgaaagg cta    13

<210> SEQ ID NO 14
<211> LENGTH: 13
<212> TYPE: DNA
<213> ORGANISM: Canis lupus familiaris

```
<400> SEQUENCE: 14
aggcgaaagg acc                                                          13

<210> SEQ ID NO 15
<211> LENGTH: 13
<212> TYPE: DNA
<213> ORGANISM: Equus ferus caballus

<400> SEQUENCE: 15
aggtgaaagg gca                                                          13

<210> SEQ ID NO 16
<211> LENGTH: 13
<212> TYPE: DNA
<213> ORGANISM: Didelphis virginiana

<400> SEQUENCE: 16
agataaaagg aca                                                          13

<210> SEQ ID NO 17
<211> LENGTH: 13
<212> TYPE: DNA
<213> ORGANISM: Artificial sequence
<220> FEATURE:
<223> OTHER INFORMATION: Synthetic polynucleotide

<400> SEQUENCE: 17
aggtgaaatt taa                                                          13
```

METHODS FOR TREATING METABOLIC DISORDERS USING FGF

CROSS-REFERENCES TO RELATED APPLICATIONS

This application is a divisional of U.S. Ser. No. 13/641,451, filed Jan. 2, 2013, which is the US National Stage of PCT application no. PCT/US2011/032848, filed Apr. 18, 2011, which claims priority to U.S. Ser. No. 61/325,255; U.S. Ser. No. 61/325,261; and U.S. Ser. No. 61/325,253, all filed Apr. 16, 2010, the disclosures of each of which are incorporated herein by reference in their entireties.

STATEMENT AS TO RIGHTS TO INVENTIONS MADE UNDER FEDERALLY SPONSORED RESEARCH OR DEVELOPMENT

This invention was made with government support under Grant Nos. DK062434, DK057978, DK090962, DK063491 and HL105278 awarded by the National Institutes of Health (NIH). The Government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 92150-897563.txt, created on Jan. 14, 2014, 3,913 bytes, machine format IBM-PC, MS-Windows operating system, is hereby incorporated by reference.

BACKGROUND OF THE INVENTION

Metabolic disorders such as type 2 diabetes, obesity, and all of the related complications, are leading causes of mortality. These disorders are associated with the excessive nutritional intake and lack of exercise of the Western lifestyle, and increasingly that of the rest of the world. Type 2 diabetes is a debilitating disease characterized by high-circulating blood glucose, insulin, and corticosteroid levels. The incidence of type 2 diabetes is high and rising and is becoming a leading cause of mortality, morbidity, and healthcare expenditure throughout the world (Amos et al., *Diabetic Med.* 14:S1-85, 1997). Diabetes (and insulin resistant conditions) result in elevated levels of glucose in the blood. Prolonged high blood sugar may cause blood vessel and nerve damage.

Various pharmacological approaches for the treatment of type 2 diabetes are available (Scheen et al., Diabetes Care, 22(9):1568-1577, 1999). One such approach is the use of thiazolidinediones (TZDs), which represent a new class of oral antidiabetic drugs that improve metabolic control in patients with type 2 diabetes. TZDs (including rosiglitazone (Avandia®) and pioglitazone (Actos®)) command a large share of the current antidiabetic drug market. TZDs reduce insulin resistance in adipose, muscle, and liver tissues (Oakes et al., Metabolism 46:935-942, (1997); Young et al. Diabetes 44:1087-1092, (1995); Oakes et al., Diabetes 43:1203-1210, (1994); Smith et al., Diabetes Obes Metab 2:363-372 (2000)). TZDs also lower the levels of free fatty acid (FFA) and triglycerides.

TZDs administered alone or in combination with metformin have glucose-lowering effects in patients with type 2 diabetes and reduce plasma insulin concentrations (i.e., in hyperinsulinaemia) (Aronoff et al., Diabetes Care 2000; 23: 1605-1611; Lebovitz et al., J Clin Endocrinol Metab 2001; 86: 280-288; Phillips et al. Diabetes Care 2001; 24: 308-315). Abnormalities in lipid levels can also be treated (Day, Diabet Med 1999; 16: 179-192; Ogihara et al. Am J Hypertens 1995; 8: 316-320), high blood pressure (Ogihara et al. Am J Hypertens 1995; 8: 316-320) and impaired fibrinolysis (Gottschling-et al. Diabetologia 2000; 43:377-383). However, there are numerous side effects associated with the use of TZDs, such as weight gain, liver toxicity, cardiovascular toxicity, upper respiratory tract infection, headache, back pain, hyperglycemia, fatigue, sinusitis, diarrhea, hypoglycemia, mild to moderate edema, fluid retention, and anemia (Moller, Nature, 2001, 414: 821-827). Accordingly, there is a need for improved therapeutic approaches to metabolic disorders that have fewer adverse effects than the available pharmaceutical approaches utilizing TZDs.

BRIEF SUMMARY OF THE INVENTION

Provided herein are compositions and methods for treating a metabolic disorder in an individual using an FGF-1 compound. Thus, in some embodiments, the invention provides pharmaceutical compositions for treating a metabolic disorder comprising an FGF-1 compound. In some embodiments, the FGF-1 compound is a functional fragment of FGF-1 (e.g., amino acids 1-140, 1-141, 14-135, etc.). In some embodiments, the FGF-1 compound is a functional analog of FGF-1. In some embodiments, the FGF-1 compound is a functional variant of FGF-1. In some embodiments, the FGF-1 compound is an expression vector comprising a sequence encoding the FGF-1 compound.

In some embodiments, the pharmaceutical composition is formulated for intravenous administration. In some embodiments, the pharmaceutical composition is formulated for subcutaneous or intraperitoneal administration. In some embodiments, the pharmaceutical composition is formulated for a dose of the FGF-1 compound equivalent to 0.01-1 mg FGF-1 per kg body weight of the individual, e.g., equivalent to 0.05-0.1, 0.1-0.2, 0.1-0.4, 0.05, 0.1, 0.2, 0.3, 0.4. 0.5 or higher mg FGF-1 per kg body weight. In some embodiments, the composition includes a second therapeutic agent, e.g., a TZD.

In some embodiments, the metabolic disorder is selected from the group consisting of elevated blood glucose (e.g., reduced ability to normalize glucose), impaired glucose tolerance, insulin resistance, type II diabetes, obesity, elevated percent body fat, and fatty liver (hepatic steatosis). In some embodiments, the metabolic disorder is obesity. In some embodiments, the individual has a BMI of 25 or higher, e.g., 26, 28, 30 or greater than 30. In some embodiments, the metabolic disorder is hepatic steatosis. In some embodiments, the metabolic disorder is insulin resistance. In some embodiments, the metabolic disorder is impaired glucose tolerance.

In some embodiments, the invention provides methods of making a medicament for use in treating a metabolic disorder comprising an FGF-1 compound as described herein. Further provided is use of an FGF-1 compound for treating a metabolic disorder in an individual.

Also provided are methods of treating a metabolic disorder in an individual (treating an individual with a metabolic disorder) comprising administering an FGF-1 compound to the individual, thereby treating the metabolic disorder. The metabolic disorder can be selected from the group consisting of elevated blood glucose (e.g., reduced ability to normalize glucose), impaired glucose tolerance, insulin resistance, type II diabetes, obesity, elevated percent body fat, and fatty liver (hepatic steatosis). In some embodiments, the metabolic disorder is obesity. In some embodiments, the individual has a BMI of 25 or higher, e.g., 26, 28, 30 or greater than 30. In some embodiments, the metabolic disorder is hepatic steatosis. In some embodiments, the metabolic disorder is insulin resistance. In some embodiments, the metabolic disorder is impaired glucose tolerance.

In some embodiments, the FGF-1 compound is a functional fragment of FGF-1 (e.g., amino acids 1-140, 1-141, 14-135, etc.). In some embodiments, the FGF-1 compound is a functional analog of FGF-1. In some embodiments, the FGF-1 compound is a functional variant of FGF-1. In some embodiments, the FGF-1 compound is an expression vector comprising a sequence encoding the FGF-1 compound.

In some embodiments, the administering is intravenous. In some embodiments, the administering is subcutaneous or intraperitoneal. In some embodiments, the dose of the FGF-1 compound administered is equivalent to 0.01-1 mg FGF-1 per kg body weight of the individual, e.g., equivalent to 0.05-0.1, 0.1-0.2, 0.1-0.4, 0.05, 0.1, 0.2, 0.3, 0.4. 0.5 or higher mg FGF-1 per kg body weight. In some embodiments, the FGF-1 compound is administered once per day or less, e.g., every second day, every third day, every week, every other week, or less.

In some embodiments, the method further comprises administering a second therapeutic agent to the individual. In some embodiments, the second therapeutic agent is administered at the same time (e.g., in the same composition) as the FGF-1 compound. In some embodiments, the second therapeutic agent is administered at a different time than the FGF-1 compound. In some embodiments, the second therapeutic agent is another treatment for a metabolic disorder (e.g., a TZD). In some embodiments, the second therapeutic agent targets an associated symptom, e.g., pain or high blood pressure.

Further provided are methods of inducing fatty liver in a food animal, e.g., a bird, such as duck or goose. The methods comprise inhibiting FGF-1 in a food animal. In some embodiments, the method comprises administering an effective amount of an FGF-1 inhibitor to the food animal. In some embodiments, the FGF-1 inhibitor is an antisense compound specific for FGF-1, e.g., an expression vector comprising a sequence encoding the antisense compound. In some embodiments, the FGF-1 inhibitor is an antibody (e.g., Shi et al. (2011) *IUBMB Life* 63:129). In some embodiments, the FGF-1 inhibitor is an inhibitor of the FGF-1 signaling pathway, e.g., a MAP kinase pathway inhibitor such as PD-098059, PD-161570, PD-173074, SU5402, or SB203580. In some embodiments, the FGF-1 inhibitor is administered more than once, e.g., once/day, or with food. In some embodiments, the FGF-1 inhibitor is administered in combination with a high fat diet. In some embodiments, the method comprises generating an FGF-1 knockout or genetically altered FGF-1 inactive food animal, and feeding the animal with a high fat diet.

DETAILED DESCRIPTION OF THE INVENTION

I. Introduction

Figure 1:
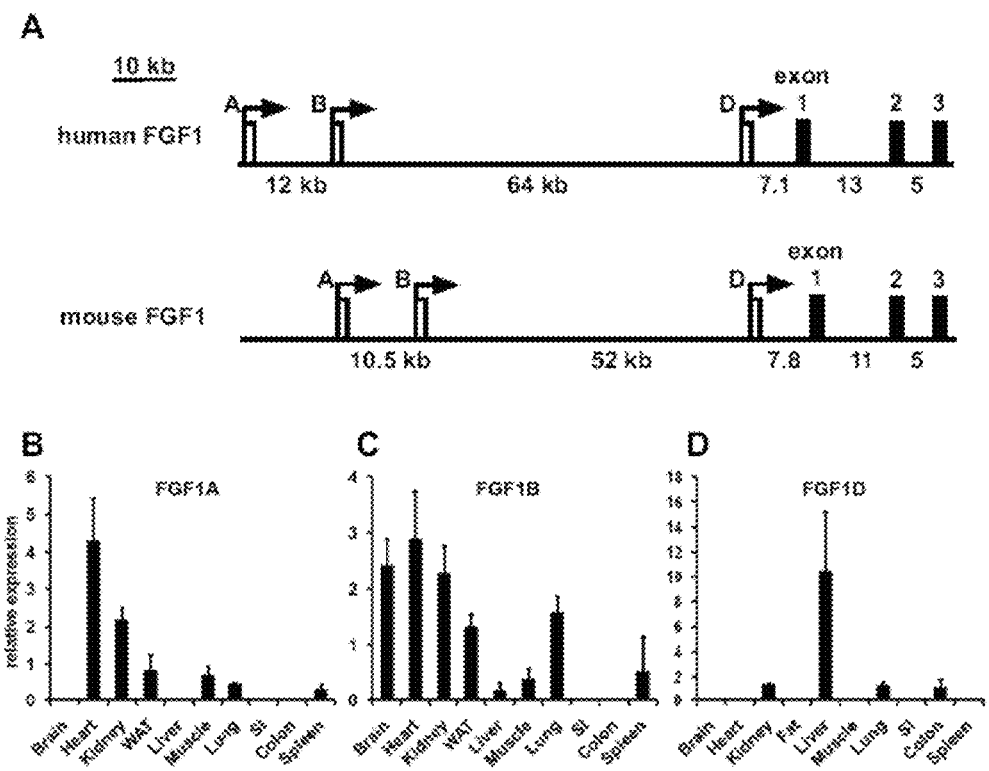
FIG. 1. FGF-1 gene structure and expression. (A) The expression of the FGF-1 gene is directed by three distinct promoters driving the untranslated exons: 1A, 1B, and 1D (open bars), spaced up to 70 kb apart. Alternative splicing of these untranslated exons to the three coding exons (closed bars) of the FGF-1 gene results in identical but differentially expressed FGF-1 polypeptides. This organization as shown for human and mouse is evolutionary conserved. Tissue distribution mRNA in mice for (B) FGF-1A, (C) FGF-1B, and (D) FGF-1D.

Provided herein are methods and compositions useful for treating metabolic disorders using FGF-1 and functional variants thereof. The inventors have shown that FGF-1 has rapid and long-lasting effects, including normalizing blood glucose, increasing insulin sensitivity, reducing percent body fat and overall body weight, increasing percent lean mass, and reducing fatty liver (hepatic steatosis).

II. Definitions

The following abbreviations are used herein:
FGF fibroblast growth factor
NHR nuclear hormone receptor
PPAR peroxisome proliferator-activated receptor
PPRE PPAR response element
TSS transcription start site
TZD thiazolidinedione
BAT brown adipose tissue
WAT white adipose tissue
HFD high fat diet
i.p. intraperitoneal injection
s.c. subcutaneous injection
p.o. oral administration
i.v. intravenous injection Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

The term FGF-1 compound refers to FGF-1 or a variant thereof (FGF-1 fragment, FGF-1 portion, modified form of FGF-1, protein having substantial identity to FGF-1, FGF-1 analog, etc.) that retains at least one FGF-1 activity (e.g., at least 10%, 20%, 30%, 40%, 50%, 60%, 70%, 80% or higher percent activity compared to FGF-1). Thus, FGF-1 compounds include functional FGF-1 fragments, functional FGF-1 variants, and functional FGF-1 analogs. An example of an FGF-1 compound that is substantially identical to FGF-1 is a protein having at least 80%, 85%, 90%, 95%, 98%, 99%, or 100% amino acid identity to FGF-1. In some embodiments, the FGF-1 compound comprises a polypeptide having, e.g., 95%, 98%, 99% or higher % identity to FGF-1, where the non-identities represent conservative substitutions or additions or deletions that do not substantially change the activity.

FGF-1 (or acidic FGF) is a secreted protein that binds heparin (e.g., heparin sulfate) and FGF receptor family members 1 and 4. The human protein is 155 amino acids in length, and the sequence is publically available at SwissProt accession number P05230.1. The term "FGF-1" refers to naturally-occurring, isolated, recombinant, or synthetically-produced proteins. FGF-1 also includes allelic variants and species homologs.

FGF-1 activities include binding heparin, FGFR1, and FGFR4, and increasing expression of GLUT1 and/or GLUT4. FGF-1 activities also include (among others) reducing glucose levels, improving glucose tolerance, and increasing insulin sensitivity in a diabetic individual. Additional FGF-1 activities include reducing percent body fat, fatty liver disease, and increasing percent lean mass in an individual.

A functional FGF-1 fragment is a protein having less than the full length sequence of FGF-1 but retaining at least 25, 50, or 80% activity of at least one FGF-1 activity (e.g., FGF-1 (14-135, 1-140, 13-135, 1-141, etc.). The functional FGF-1 fragment can have an amino acid sequence of any length up to the full length FGF polypeptide sequence, e.g., 50, 50-80, 50-100, 120-150, 100-150, or more than 100 amino acids. In some embodiments, the functional FGF fragment is at least 80%, 85%, 90%, 95%, 98%, or 100% identical to FGF-1 over the covered portion of the full length sequence (e.g., over 50-150 amino acids). In some embodiments, the functional FGF-1 fragment has greater than 90%, e.g., 95%, 98%, 99% or higher % identity to FGF-1 1-141. In some embodiments, the functional FGF-1 fragment has greater than 90%, e.g., 95%, 98%, 99% or higher % identity to FGF-1 1-141, where the non-identities represent conservative substitutions or additions or deletions that do not substantially change the activity.

A functional FGF-1 analog is a modified or synthetic (e.g., peptidomimetic) form of FGF-1 that retains at least 25, 50, or 80% activity of at least one FGF-1 activity. Examples of FGF-1 analogs that retain heparin-binding activity are disclosed in WO2006/093814. The FGF-1 analog can include non-naturally occurring amino acids, or modified amino acids, e.g., that improve the stability (in storage or in vivo) or pharmacological properties (tissue profile, half-life, etc.) of the protein. The functional FGF-1 analog can also be a functional FGF-1 variant, e.g., having greater than 90%, e.g., 95%, 98%, 99% or higher % identity to FGF-1. In some embodiments, the functional FGF-1 analog has at least 95%, 98%, 99% or higher % identity to FGF-1, where the non-identities represent conservative substitutions or additions or deletions that do not substantially change the activity.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The words "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following amino acids are typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "identical" or percent "identity," in the context of two or more nucleic acids, or two or more polypeptides, refer to two or more sequences or subsequences that are the same or have a specified percentage of nucleotides, or amino acids, that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the compliment of a nucleotide test sequence. The definition also includes sequences that have deletions and/or additions, as well as those that have substitutions. Algorithms can account for gaps and the like. Identity generally exists over a region that is at least about 25 amino acids or nucleotides in length, or over a region that is 50-100 amino acids or nucleotides in length.

The term "metabolic disorder" is used broadly herein to refer to the conditions, diseases, and disorders associated with insulin and/or glucose dysregulation. Metabolic disorders include type 2 diabetes, insulin insensitivity, glucose intolerance, elevated blood glucose levels, obesity, high percent body fat, fatty liver, etc. One of skill will understand that metabolic disorders are associated with and can result in a wide range of other disorders, e.g., high blood pressure, heart disease, poor circulation, etc., which can be ameliorated by addressing the metabolic disorder according to the methods of the invention.

"Biopsy" or "biological sample from a patient" as used herein refers to a sample obtained from a patient having, or suspected of having, a metabolic disorder. In some embodiments, the biopsy is a blood sample, which can be separated into blood components (plasma, serum, white blood cells, red blood cells, platelets, etc.). In some embodiments, the sample is a tissue biopsy, such as needle biopsy, fine needle biopsy, surgical biopsy, etc. Tissue samples can be obtained from adipose, muscle, liver, etc.

A "biological sample" or "cellular sample" can be obtained from a patient, e.g., a biopsy, from an animal, such as an animal model, or from cultured cells, e.g., a cell line or cells removed from a patient and grown in culture for observation. Biological samples include tissues and bodily fluids, e.g., blood, blood fractions, lymph, saliva, urine, feces, etc.

"Subject," "patient," "individual" and like terms are used interchangeably and refer to, except where indicated, mammals such as humans and non-human primates, as well as livestock and companion animals. The term does not necessarily indicate that the subject has been diagnosed with a metabolic disorder, but typically refers to an individual under medical supervision. A patient can be an individual that is seeking treatment, monitoring, adjustment or modification of an existing therapeutic regimen, etc. The terms can refer to an individual that has been diagnosed, is currently following a therapeutic regimen, or is at risk of developing a metabolic disorder, e.g., due to family history, sedentary lifestyle, etc.

A "control" condition or sample refers to a sample that serves as a reference, usually a known reference, for comparison to a test condition or sample. For example, a test sample can represent a patient sample, while a control can represent a sample from an individual known to have a metabolic disorder, or from an individual that is known to not have the disorder. In another example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The terms "therapy," "treatment," and "amelioration" refer to any reduction in the severity of symptoms. In the case of treating metabolic disorders, the terms can refer to reducing blood glucose, increasing insulin sensitivity, reducing body weight, reducing percent body fat, increasing percent lean mass, reducing side effects of associated therapies, etc. As used herein, the terms "treat" and "prevent" are not intended to be absolute terms. Treatment can refer to any delay in onset, amelioration of symptoms, improvement in patient survival, increase in survival time or rate, etc. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The terms "effective amount," "effective dose," "therapeutically effective amount," etc. refer to that amount of the therapeutic agent sufficient to ameliorate a disorder, as described above. For example, for the given parameter, a therapeutically effective amount will show an increase or decrease of therapeutic effect at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. In the context of the present invention, the effective amount of an FGF-1 compound can vary depending on co-administration of other therapeutics or metabolic profile of the individual (among other factors such as age, severity of disease, etc.).

The term "diagnosis" refers to a relative probability a subject has a given metabolic disorder. Symptoms and diagnostic criteria are summarized below. Similarly, the term "prognosis" refers to a relative probability that a certain future outcome may occur in the subject. For example, in the context of the present invention, prognosis can refer to the likelihood that an individual will develop a metabolic disorder. Prognosis can also refer to the likely severity of the disease (e.g., severity of symptoms, rate of functional decline, survival, etc.). The terms are not intended to be absolute, as will be appreciated by any one of skill in the field of medical diagnostics.

III. Fibroblast Growth Factor (FGF)-1

Fibroblast growth factors (FGFs) are a family of distinct polypeptide hormones that are widely expressed in developing and adult tissues (Baird et al., *Cancer Cells*, 3:239-243, 1991). FGFs play crucial roles in multiple physiological functions including angiogenesis, development, mitogenesis, pattern formation, cellular proliferation, cellular differentiation, metabolic regulation, and repair of tissue injury (McKeehan et al., *Prog. Nucleic Acid Res. Mol. Biol.* 59:135-176, 1998; Beenken and Mohammadi, 2009). The FGF family now consists of at least twenty-three members, FGF-1 to FGF-23 (Reuss et al., *Cell Tissue Res.* 313:139-157 (2003).

FGFs bind to FGF receptors (FGFRs), of which there are four (FGFR1-4). The receptor binding specificity of each FGF is distinct, and can also depend on the particular isoform of the FGFR. For example FGFR1 has at least 3 isoforms that result in different splice variants in the third Ig-like domain (Lui et al. (2007) *Cancer Res.* 67:2712). FGF signaling is also determined by the tissue specificity of the receptor and receptor isoform. FGF-1 can bind to all FGFRs, but is reported to be internalized only upon binding to FGFR1 and FGFR4. A review of FGF-FGFR specificities can be found, e.g., in Sørensen et al. (2006) *J Cell Science* 119:4332.

The polypeptide and coding sequences of FGF-1 are known for a number of animals and publically available from the NCBI website. FGF-1 compounds that can be used in the methods of the invention include full length human FGF-1, species homologs thereof, and functional fragments thereof. Additional FGF-1 compounds that can be used include modified versions of FGF-1 (e.g., modified to increase stability, e.g., PEGylated or including non-naturally occurring amino acids), functional analogs of FGF-1, and functional FGF-1 variants with substantial identity to FGF-1. Another FGF-1 compound that can be used in the present methods includes expression vectors for stable or transient expression of FGF-1 in a cell. FGF-1 compounds include those that retain at least one FGF-1 activity, e.g., binding heparin, FGFR1, and FGFR4, and increasing expression of GLUT1 and/or GLUT4. FGF-1 acitivities include (among others) reducing (normalizing) glucose levels, improving glucose tolerance, and increasing insulin sensitivity in a diabetic individual. Additional FGF-1 activities include reducing percent body fat, fatty liver disease, and increasing percent lean mass in an individual.

In some embodiments, the FGF-1 compound is a functional FGF-1 variant, functional FGF-1 fragment, and/or functional FGF-1 analog. That is, the FGF-1 compound can be a functional FGF-1 fragment with variations and modified or non-naturally occurring amino acids, as long as the FGF-1 compound retains at least one FGF-1 activity. In some embodiments, the FGF-1 compound is substantially identical to full length FGF-1 or a fragment thereof, e.g., at least 95, 98, or 99% identical over the relevant length of FGF-1, where the non-identities include conservative substitutions or deletions or additions that do not affect the FGF-1 activity. Examples of FGF-1 amino acids that are involved in FGF-1 activities, and thus less amenable to substitution or deletion, include Tyr-15, Arg-35, Asn-92, Tyr-94, Lys-101, His-102, Trp-107, Leu-133, and Leu-135. Also included are Lys-112, Lys-113, Lys-118, Arg-122, and Lys-128, which are involved in heparin interactions. The position of these residues is with reference to the 155 amino acid human sequence, but can be determined for species homologs.

In some embodiments, the FGF-1 compound comprises amino acids 1-140 of FGF-1, or a sequence having at least 90% identity to amino acids 1-140 of FGF-1 that retains at least one FGF-1 activity. In some embodiments, the FGF-1 activity is normalizing blood glucose levels in an individual. In some embodiments, the FGF-1 activity is reducing percent body fat in an individual. In some embodiments, the FGF-1 activity is increasing insulin sensitivity in an individual. In some embodiments, the FGF-1 activity is binding to FGFR1 or FGFR4. In some embodiments, the FGF-1 activity is increasing expression of GLUT1.

The FGF-1 compound may be generated, isolated, and/or purified by any means known in the art. For standard recombinant methods, see Sambrook et al., Molecular Cloning: A Laboratory Manual, Cold Spring Harbor Laboratory Press, NY (1989); Deutscher, Methods in Enzymology 182: 83-9 (1990); Scopes, Protein Purification: Principles and Practice, Springer-Verlag, NY (1982).

The FGF-1 compound can be modified, e.g., to improve stability or its pharmacological profile. Chemical modifications include, e.g., adding chemical moieties, creating new bonds, and removing chemical moieties. Modifications at amino acid side groups include acylation of lysine ϵ-amino groups, N-alkylation of arginine, histidine, or lysine, alkylation of glutamic or aspartic carboxylic acid groups, and deamidation of glutamine or asparagine. Modifications of the terminal amino group include the des-amino, N-lower alkyl, N-di-lower alkyl, and N-acyl modifications. Modifications of the terminal carboxy group include the amide, lower alkyl amide, dialkyl amide, and lower alkyl ester modifications.

Examples of compounds that can improve the pharmacological profile of the FGF-1 compound include water soluble polymers, such as PEG, PEG derivatives, polyalkylene glycol (PAG), polysialyic acid, hydroxyethyl starch, peptides (e.g., Tat (from HIV), Ant (from the *Drosophila antennapedia* homeotic protein), or poly-Arg), and small molecules (e.g., lipophilic compounds such as cholesterol or DAG).

In some embodiments, the FGF-1 is linked to a heparin molecule, which can improve the stability of FGF-1, and prevent interaction with heparin in vivo. Linking heparin to FGF-1 ensures that more of the modified FGF-1 remains in circulation than it would without the heparin modification.

The FGF-1 compound can be expressed recombinantly using routine techniques in the field of recombinant genetics. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook and Russell eds. (2001) Molecular Cloning: A Laboratory Manual, 3rd edition; the series Ausubel et al. eds. (2007 with updated through 2010) Current Protocols in Molecular Biology, among others known in the art.

To obtain high level expression of a nucleic acid sequence, such as the nucleic acid sequences encoding an FGF-1 compound, one typically subclones a nucleic acid sequence that encodes a polypeptide sequence of the invention into an expression vector that is subsequently transfected into a suitable host cell. The expression vector typically contains a strong promoter or a promoter/enhancer to direct transcription, a transcription/translation terminator, and for a nucleic acid encoding a protein, a ribosome binding site for translational initiation. The promoter is operably linked to the nucleic acid sequence encoding a polypeptide of the invention or a subsequence thereof.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to the recombinant polypeptides to provide convenient methods of isolation, e.g., His tags. In some case, enzymatic cleavage sequences (e.g., Met-(His)$_g$-Ile-Glu-GLy-Arg which form the Factor Xa cleavage site) are added to the recombinant polypeptides. Bacterial expression systems for expressing the polypeptides are available in, e.g., *E. coli*, *Bacillus* sp., and *Salmonella* (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available.

Standard transfection methods can be used to produce cell lines that express large quantities of polypeptides of the invention, which are then purified using standard techniques (see, e.g., Colley et al., *J. Biol. Chem.,* 264:17619-17622 (1989); Guide to Protein Purification, in Methods in Enzymology, vol. 182 (Deutscher, ed., 1990)). Transformation of cells is performed according to standard techniques (see, e.g., Morrison, *J. Bact.,* 132:349-351 (1977); Clark-Curtiss & Curtiss, Methods in Enzymology, 101:347-362 (Wu et al., eds, 1983). For example, any of the well known procedures for introducing foreign nucleotide sequences into host cells may be used. These include the use of calcium phosphate transfection, polybrene, protoplast fusion, electroporation, liposomes, microinjection, plasma vectors, and viral vectors (see, e.g., Sambrook et al., supra).

FGF-1 can be purified to substantial purity by standard techniques known in the art, including, for example, extraction and purification from inclusion bodies, size differential filtration, solubility fractionation (i.e., selective precipitation with such substances as ammonium sulfate); column chromatography, immunopurification methods, etc.

The FGF-1 compound can also be chemically synthesized using known methods including, e.g., solid phase synthesis (see, e.g., Merrifield, *J. Am. Chem. Soc.,* 85:2149-2154 (1963) and Abelson et al., Methods in Enzymology, Volume 289: Solid-Phase Peptide Synthesis (1st ed. 1997)). Polypeptide synthesis can be performed using manual techniques or by automation. Automated synthesis can be achieved, for example, using Applied Biosystems 431A Peptide Synthesizer (Perkin Elmer). Alternatively, various fragments of the polypeptide (and any modified amino acids) can be chemically synthesized separately and then combined using chemical methods to produce the full length polypeptide. The sequence and mass of the polypeptides can be verified by GC mass spectroscopy. Once synthesized, the polypeptides can be modified, for example, by N-terminal acetyl- and C-terminal amide-groups as described above. Synthesized polypeptides can be further isolated by HPLC to a purity of at least about 80%, preferably 90%, and more preferably 95%.

The invention further provides methods of inhibiting FGF-1 to induce fatty liver in a food animal, e.g., a bird such as a duck, goose, quail, etc. The inhibited expression or activity can be 40%, 50%, 60%, 70%, 80%, 90% or less than that in a untreated or wild type control. In certain instances, the inhibition is 1.5-fold, 2-fold, 3-fold, 4-fold, 5-fold, 10-fold, or more in comparison to a control.

Typically, inhibition of FGF-1 is accompanied by a high fat diet. In some cases, the method comprises generating a genetically modified animal with defective FGF-1 activity (e.g., an FGF-1 knockout animal). In some embodiments, FGF-1 is inhibited by administering an FGF-1 inhibitor to the animal. Typically, the inhibitor is administered more than once, e.g., on a regular schedule (daily, weekly, etc.) or with food.

The FGF-1 inhibitor can be an antisense compound. The term "antisense" is used herein as a general term referring to RNA targeting strategies for reducing gene expression. Antisense includes RNAi, siRNA, shRNA, etc. Typically, the antisense sequence is identical to the targeted sequence (or a fragment thereof), but this is not necessary for effective reduction of expression. For example, the antisense sequence can have 85, 90, 95, 98, or 99% identity to the complement of a target RNA or fragment thereof. The targeted fragment can be about 10, 20, 30, 40, 50, 10-50, 20-40, 20-100, 40-200 or more nucleotides in length.

The term "RNAi" refers to RNA interference strategies of reducing expression of a targeted gene. RNAi technique employs genetic constructs within which sense and anti-sense sequences are placed in regions flanking an intron sequence in proper splicing orientation with donor and acceptor splicing sites. Alternatively, spacer sequences of various lengths can be employed to separate self-complementary regions of sequence in the construct. During processing of the gene construct transcript, intron sequences are spliced-out, allowing sense and anti-sense sequences, as well as splice junction sequences, to bind forming double-stranded RNA. Select ribonucleases then bind to and cleave the double-stranded RNA, thereby initiating the cascade of events leading to degradation of specific mRNA gene sequences, and silencing specific genes. The phenomenon of RNA interference is described and discussed in Bass, *Nature* 411: 428-29 (2001); Elbahir et al., *Nature* 411: 494-98 (2001); and Fire et al., *Nature* 391: 806-11 (1998); and WO 01/75164, where methods of making interfering RNA also are discussed.

The term "siRNA" refers to small interfering RNAs, that are capable of causing interference with gene expression and can cause post-transcriptional silencing of specific genes in cells, for example, mammalian cells (including human cells) and in the body, for example, in a mammal (including humans). The siRNAs based upon the sequences and nucleic acids encoding the gene products disclosed herein typically have fewer than 100 base pairs and can be, e.g., about 30 bps or shorter, and can be made by approaches known in the art, including the use of complementary DNA strands or synthetic approaches. The siRNAs are capable of causing interference and can cause post-transcriptional silencing of specific genes in cells, for example, mammalian cells (including human cells) and in the body, for example, in a mammal (including humans). Exemplary siRNAs have up to 40 bps, 35 bps, 29 bps, 25 bps, 22 bps, 21 bps, 20 bps, 15 bps, 10 bps, 5 bps or any integer thereabout or therebetween. Tools for designing optimal inhibitory siRNAs include that available from DNAengine Inc. (Seattle, Wash.) and Ambion, Inc. (Austin, Tex.).

A "short hairpin RNA" or "small hairpin RNA" is a ribonucleotide sequence forming a hairpin turn which can be used to silence gene expression. After processing by cellular factors the short hairpin RNA interacts with a complementary RNA thereby interfering with the expression of the complementary RNA.

The FGF-1 inhibitor can also be an antibody that interferes with FGF-1 signaling, e.g., a FGF-1 specific antibody, or a functional fragment thereof. An example of an FGF-1 antibody is described, e.g., in Shi et al. (2011) *IUBMB Life* 63:129, but several are commercially available. Antibodies can exist as intact immunoglobulins or as any of a number of well-characterized fragments that include specific antigen-binding activity. Typically, the "variable region" of the antibody contains the antigen-binding activity, and is most critical in specificity and affinity of binding. See Paul, *Fundamental Immunology* (2003). Such fragments can be produced by digestion with various peptidases. Pepsin digests an antibody below the disulfide linkages in the hinge region to produce $F(ab)'_2$, a dimer of Fab which itself is a light chain joined to $V_H$-$C_H 1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. The term antibody includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

The FGF-1 inhibitor can also be an inhibitor of the FGF-1 signaling pathway, e.g., a MAP kinase pathway inhibitor such as PD-098059, PD-161570, SU5402, or SB203580.

IV. Metabolic Disorders Amenable to Treatment with an FGF-1 Compound

The FGF-1 compound described herein can be used to treat metabolic disorders, e.g., type 2 diabetes, insulin insensitivity, glucose intolerance, metabolic syndrome, fatty liver disease, obesity, and conditions related thereto. Related to the obesity application, the FGF-1 compound can also be used to reduce percentage body fat and/or increase the percentage of lean mass in an individual. Conditions related to the metabolic disorders, that can also benefit from treatment with and FGF-1 compound include high blood pressure (hypertension), cardiovascular disease, hyperglycemia, hyperuricemia, and polycystic ovary syndrome.

Metabolic syndrome (also known as metabolic syndrome X or syndrome X) is a combination of medical disorders that increases the risk of cardiovascular disease. In general, a diagnosis of metabolic syndrome requires at least three of the following criteria (see International Diabetes Foundation (IDF) and U.S. National Cholesterol Education Program (NCEP)):

Central obesity: waist circumference ≥40 inches (male), ≥36 inches (female)
BMI: >30 kg/m$^2$
Elevated triglycerides (dyslipidaemia): >150 mg/dL
Lowered HDL cholesterol: <40 mg/dL (males), <50 mg/dL (females)
Raised blood pressure (BP) (hypertension): systolic BP>130 or diastolic BP>85 mm Hg
Raised fasting plasma glucose (FPG): >100 mg/dL Elevated LDL cholesterol is marked by levels above about 100, about 130, about 160 or about 200 mg/dL. Metabolic syndrome may also be related to elevated total cholesterol.

Impaired glucose intolerance is defined as a two-hour glucose levels (glycemia) of about 140 to about 199 mg/dL (7.8 to 11.0 mmol) on the 75-g oral glucose tolerance test (according to WHO and ADA). Glycemia of about 200 mg/dl or greater is considered diabetes mellitus.

Hyperglycemia, or high blood sugar, can be defined as a blood glucose level higher than about 7, about 10, about 15, or about 20 mmol/L.

Hypoglycemia, or low blood sugar, can be defined as preprandial blood glucose below about 4 or about 6 mmol/L (72 to 108 mg/dl) or 2-hour postprandial blood glucose below about 5 or about 8 mmol/L (90 to 144 mg/dl).

Insulin resistance is defined as a state in which a normal amount of insulin produces a subnormal biologic response. Insulin resistance can be measured by the hyperinsulinemic euglycemic clamp technique, Homeostatic Model Assessment (HOMA), or Quantitative insulin sensitivity check index (QUICKI).

Hyperuricemia is an abnormally high level of uric acid in the blood, e.g., above 360 µmol/L (6 mg/dL) for women and 400 µmol/L (6.8 mg/dL) for men.

Polycystic ovarian syndrome (PCOS) is associated with oligoovulation, anovulation, excess androgen, and/or polycystic ovaries. Metabolic syndrome may also be associated with acanthosis nigricans.

Metabolic syndrome may also be associated with a pro-inflammatory state (e.g., elevated C-reactive protein levels in the blood, e.g., above 10 mg/L) and microalbuminuria (urinary albumin excretion ratio ≥20 mg/min or albumin:creatinine ratio ≥30 mg/g).

In some embodiments, the FGF-1 compound can be used to treat fatty liver disease or a condition related thereto. The fatty liver disease can be a method of treating nonalcoholic steato-hepatitis (NASH), nonalcoholic fatty liver disease (NAFLD), simple fatty liver (steatosis), cirrhosis, hepatitis, liver fibrosis, or steatonecrosis. Fatty liver disease can be assessed by diagnostic methods known in the art including liver enzyme tests (ALT, AST), liver ultrasound, FibroTest®, SteatoTest®, coagulation studies including international normalized ratio (INR), as well as blood tests including M30-Apoptosense ELISA, erythrocyte sedimentation rate, glucose, albumin, and renal function.

Fatty liver disease may also be associated with a pro-inflammatory state (e.g., elevated C-reactive protein levels in the blood, e.g., above 10 mg/L) as well as hepatocellular carcinoma. Fatty liver disease may also be associated with abetalipoproteinemia, glycogen storage diseases, Weber-Christian disease, Wolman disease, acute fatty liver of pregnancy, lipodystrophy, inflammatory bowel disease, HIV, and hpatitis C (especially genotype 3), and alpha 1-antitrypsin deficiency.

In some embodiments, the FGF-1 compound is used to reduce percentage body fat, increase percentage lean mass, or to treat obesity (as well as associated conditions). The method can be used to treat class I obesity, class II obesity, class III obesity, elevated body weight, elevated body mass index (BMI), elevated body volume index (BVI), elevated body fat percentage, elevated fat to muscle ratio, elevated waist circumference, or elevated waist-hip ratio.

Class I obesity is characterized by a BMI of about 30 to about 35, class II obesity (severe obesity) is characterized by a BMI of about 35 to about 40, and class III obesity (morbid obesity) is characterized by a BMI of 40 or greater. A BMI of greater than about 45 or 50 is considered super obese. Elevated body weight can be assessed in consideration of age, gender, height, frame, and/or ethnicity.

Elevated waist-hip ratio is defined as greater than about 0.9 for men and greater than about 0.7 for women.

Metabolic disorders are inter-related and can result in disorders across various systems. Addressing the core metabolic disorder can reduce the severity of related conditions in a patient, including, e.g.:

cardiovascular disorders including, e.g., ischemic heart disease, angina and myocardial infarction, congestive heart failure, high blood pressure, abnormal cholesterol levels, deep vein thrombosis, and pulmonary embolism, neurological disorders including, e.g., stroke, meralgia paresthetica, migraines, idiopathic, and intracranial hypertension, depression (especially in women) and social stigmatism, rheumatological and orthopedic disorders including, e.g., gout, poor mobility, osteoarthritis, and lower back pain, dermatological disorders including, e.g., stretch marks, acanthosis nigricans, lymphedema, cellulitis, gastrointestinal disorders including, e.g., gastroesophageal reflux disease (GERD) and cholelithiasis (gallstones), respiratory disorders including, e.g., obstructive sleep apnea, obesity hypoventilation syndrome, asthma, and increased complications during general anaesthesia, urology and nephrology disorders including, e.g., erectile dysfunction, urinary incontinence, chronic renal failure, and hypogonadism.

V. Pharmaceutical Compositions

The FGF-1 compounds can be used and formulated into any of a number of pharmaceutical compositions, including those described in the United States Pharmacopeia (U.S.P.), *Goodman and Gilman's The Pharmacological Basis of Therapeutics*, 10$^{th}$ Ed., McGraw Hill, 2001; Katzung, Ed., *Basic and Clinical Pharmacology*, McGraw-Hill/Appleton & Lange, 8$^{th}$ ed., Sep. 21, 2000; *Physician's Desk Reference* (Thomson Publishing; and/or *The Merck Manual of Diagnosis and Therapy*, 18$^{th}$ ed., 2006, Beers and Berkow, Eds., Merck Publishing Group; or, in the case of animals, *The Merck Veterinary Manual*, 9$^{th}$ ed., Kahn Ed., Merck Publishing Group, 2005.

The compositions disclosed herein can be administered by any means known in the art. For example, compositions may include administration to a subject intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intrathecally, subcutaneously, subconjunctival, intravesicularlly, mucosally, intrapericardially, intraumbilically, intraocularly, orally, locally, by inhalation, by injection, by infusion, by continuous infusion, by localized perfusion, via a catheter, via a lavage, in a creme, or in a lipid composition. Administration can be local, e.g., to adipose tissue or to the liver, or systemic.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage can be dissolved in 1 ml of isotonic NaCl solution and either added to 1000 ml of hypodermoclysis fluid or injected at the proposed site of infusion.

Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

Heparin can interfere with FGF-1 circulation when the FGF-1 compound is not administered intravenously. For non-i.v. administration, e.g., subcutaneous administration, the FGF-1 compound can be linked to a heparin molecule, or another compound that interferes with FGF-1 binding to heparin. The FGF-1-heparin interaction in vivo reduces the amount of circulating FGF-1, and the duration of the therapeutic effect. Thus, in some embodiments, the invention provides a pharmaceutical composition comprising an FGF-1 compound linked to heparin. Diabetes medications are commonly administered s.c., thus, it can be more convenient to the patient to receive the FGF-1 compound in the same s.c. composition, or in a different composition but using a familiar route of administration.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

In some embodiments, FGF-1 is administered using a gene therapy construct, e.g., as described in Nikol et al. (2008) *Mol. Ther.* Thus, in some embodiments, an individual is treated for a metabolic disorder by administering to the individual an expression vector comprising a sequence that codes for a FGF-1 compound. Similarly, the methods of inducing fatty liver in an animal can rely on administration of an expression vector, in this case, an expression vector encoding an antisense construct specific for FGF-1.

In some cases, a polynucleotide encoding FGF-1 is introduced into a cell in vitro and the cell is subsequently introduced into a subject. In some cases, the cells are first isolated from the subject and then re-introduced into the subject after the polynucleotide is introduced. In some embodiments, FGF-1-encoding polynucleotides or FGF-1 inhibitory polynucleotides are introduced directly into cells in the subject in vivo.

Conventional viral and non-viral based gene transfer methods can be used to introduce nucleic acids encoding FGF-1 polypeptides in mammalian cells or target tissues. Such methods can be used to administer nucleic acids encoding FGF-1 polypeptides, or FGF-1 inhibitory polynucleotides to cells in vitro. In some embodiments, such polynucleotides are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, Restorative Neurology and Neuroscience 8:35-36 (1995); Kremer & Perricaudet, *British Medical Bulletin* 51(1):31-44 (1995); Haddada et al., in *Current Topics in Microbiology and Immunology* Doerfler and Böhm (eds) (1995); and Yu et al., *Gene Therapy* 1:13-26 (1994).

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described, e.g., in U.S. Pat. No. 5,049,386, U.S. Pat. No. 4,946,787; and U.S. Pat. No. 4,897,355, and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

RNA or DNA viral based systems can be used to target the delivery of polynucleotides carried by the virus to specific cells in the body and deliver the polynucleotides to the nucleus. Viral vectors can be administered directly to patients (in vivo) or they can be used to transfect cells in vitro. In some cases, the transfected cells are administered to patients (ex vivo). Conventional viral based systems for the delivery of polypeptides of the invention could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene, and high transduction efficiencies.

VI. Methods of Treatment

The invention provides methods of treating, preventing, and/or ameliorating a metabolic disorder in a subject in need thereof. The course of treatment is best determined on an individual basis depending on the particular characteristics of the subject. The treatment can be administered to the subject on a daily, twice daily, every other day, bi-weekly, weekly, monthly or any applicable basis that is therapeutically effective. The treatment can be administered alone or in combination with at least one other therapeutic agent, e.g., targeting the same metabolic disorder or a related symptom. The additional agent can be administered simultaneously with the FGF-1 compound, at a different time, or on an entirely different therapeutic schedule (e.g., the FGF-1 compound can be administered daily, while the additional agent is weekly).

The suitability of a particular route of administration will depend in part on the pharmaceutical composition, its components, and the disorder being treated. Parenteral administration is often effective for systemic treatment.

The dosage of a therapeutic agent administered to a patient will vary depending on a wide range of factors. For example, it would be necessary to provide substantially larger doses to humans than to smaller animals. The dosage will depend upon the size, age, sex, weight, medical history and condition of the patient, use of other therapies, the potency of the substance being administered, and the frequency of administration.

The dose of the FGF-1 compound can be equivalent to 0.005-1 mg FGF-1 per kg body weight. For example, the dose can be equivalent to 0.01-0.1, 0.1-0.2, 0.1-0.5. 0.2-0.5, 0.5-0.8. or 0.5 or more mg FGF-1 per kg body weight. One of skill will understand and be able to adjust to situations where the FGF-1 compound is smaller (e.g., a functional FGF-1 fragment) or larger (e.g., a modified FGF-1 polypeptide) than FGF-1.

Having indicated that there is variability in terms of dosing, it is believed that those skilled in the art can determine appropriate dosing by administering relatively small amounts and monitoring the patient for therapeutic effect. If necessary, incremental increases in the dose can be made until the desired results are obtained. Generally, treatment is initiated with smaller dosages which may be less than the optimum dose of the therapeutic agent. Thereafter, the dosage is increased by small increments until the optimum effect under circumstances is reached. The total daily dosage can be divided and administered in portions during the day if desired.

The pharmaceutical preparation can be packaged or prepared in unit dosage form. In such form, the preparation is subdivided into unit doses containing appropriate quantities of the active component, e.g., according to the dose of the therapeutic agent. The unit dosage form can be a packaged preparation, the package containing discrete quantities of preparation. The composition can, if desired, also contain other compatible therapeutic agents.

In some embodiments, the FGF-1 compound is co-administered with at least one additional therapeutic agent, e.g., another therapeutic agent for treating a metabolic disorder, or a therapeutic agent to address associated symptoms, e.g., a blood thinner or analgesic. Therapeutic agents commonly used for metabolic disorders include drugs from the following classes: alpha-glucosidase inhibitors, amylin agonists, dipeptidyl-peptidase 4 (DPP-4) inhibitors, meglitinides, sulfonylureas and PPAR agonists such as thiazolidinediones (TZD). The PPAR agonist, e.g., PPARγ agonist, can include, e.g., aleglitazar, farglitazar, muraglitazar, tesaglitazar, and thiazolidinedione (TZD). Exemplary TZDs include pioglitazone (Actos®), rosiglitazone (Avandia®), rivoglitazone, and troglitazone (Hauner, *Diabetes Metab Res Rev* 18:S10-S15 (2002)).

Additional complementary active agents, such as biguanides (e.g., metformin) or sulfonylureas, can also be used in appropriate circumstances.

The combination of an FGF-1 compound with another therapeutic agent can result in a synergistic effect with enhanced efficacy in the treatment of metabolic disorders such as type 2 diabetes and related conditions. The synergy allows for reduced dosages of the active agents in combination as compared to the dosages for either active individually. The reduced dosage can help reduce any side effects that may appear.

Accordingly, in combination therapy, the effective amount of the additional (second) therapeutic agent and the effective amount of the FGF-1 compound are together effective to reduce the symptoms/effects of metabolic disorder. In some embodiments, the combination is an FGF-1 compound and TZD. The FGF/TZD combination allows for a reduced dose of TZD required for therapeutic treatment of type 2 diabetes, thereby minimizing the side effects typically observed with TZD therapy. For example the amount of TZD administered in combination with the FGF-1 compound is reduced by about 10%, 20%, 30%, 40%, 50%, 60%, 70%, or to about 80% compared to the typical dose of TZD utilized in the treatment of type 2 diabetes.

One of skill in medicine can best determine the appropriate dose of the additional therapeutic agent by considering the state of the patient, the recommended dose, the severity of disease, and the synergistic effect of the FGF compound. For example, the amount of rosiglitazone can be about 4 mg to about 8 mg per day (e.g., about 2 mg, about 4 mg, or about 8 mg per dose). The amount of pioglitazone can be about 15 mg to about 45 mg per day, e.g., about 30 mg per day.

The following discussion of the invention is for the purposes of illustration and description, and is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. All publications, patents, patent applications, Genbank numbers, and websites cited herein are hereby incorporated by reference in their entireties for all purposes.

VII. Examples

Materials and Methods

Animals. The animals that were used were FGF-1$^{-/-}$ (Miller et al., 2000), PPARγ$^{f/f}$/aP2-Cre mice (He et al., 2003) and wild-type littermate controls of a >99% C57/B6 genetic background.

Ob/ob male mice (8 wks old, B6.Cg-Lep$^{ob}$ Ldlr$^{tm1Her}$/J) were from Jackson labs. The Ob/ob mouse model is an animal model for hyperglycemia, insulin resistance, and obesity. Male ob/ob mice are used to monitor plasma glucose levels, lipid levels, etc.

Animals were kept in a temperature-controlled environment with a 12-hour light/12-hour dark cycle. They received a standard diet (MI laboratory rodent diet 5001, Harlan Teklad) or high fat (60%), high carbohydrate (HFD) diet (F3282, Bio-Serv), and acidified water ad libitum.

Cell Culture.

3T3-L1 mouse pre-adipocytes were from American Type Culture Collection (ATCC, Rockville, Md.). Cells were maintained at sub-confluence in growth medium (GM) containing 10% calf serum in Dulbecco's modified Eagle's medium (DMEM) at 37° C. and 5% $CO_2$. For standard adipocyte differentiation, cells were stimulated at 2 days post confluency (referred as day 0) with differentiation medium (DM) containing 10% fetal bovine serum (FBS), 5 µg/ml insulin, 1 µM dexamethasone, and 0.5 µM 3-isobutyl-1-methylxanthine (IBMX) for 48 hours. Then, the medium was replaced with DMEM 10% FBS with 5 µg/ml insulin for an additional 48 hours. Then, the cells were maintained in post differentiation medium containing 10% FBS. CV-1 cells were used for luciferase reporter assays. CV-1 cells were cultured in DMEM medium with 10% fetal bovine serum at 37° C. and 5% $CO_2$.

Western Analysis.

Total cell lysates from tissues were prepared as described. Western blotting was performed as described using polyclonal goat anti-human FGF-1 (C-19) antibody (1:200, Santa Cruz), anti-AKT (1:1000, Cell Signaling Technology, 9272), monoclonal rabbit anti-GSK3b (1:1000, Cell Signaling Technology, 9315), and polyclonal rabbit anti-p44/42 MAPK (1:1000, Cell Signaling Technology, 9102). Antibody binding was detected using peroxidase-conjugated donkey anti-goat IgG (1:5000, Santa Cruz).

Serum Analysis.

Blood was collected by tail bleeding either in the ad libitum fed state or following overnight fasting. Free fatty acids (Wako), triglycerides (Thermo), and cholesterol (Thermo) were measured using enzymatic colorimetric methods following the manufacturer's instructions. Serum insulin levels were measured using an Ultra Sensitive Insulin ELISA kit (Crystal Chem). Serum adiponectin levels were measured by ELISA (Millipore). Plasma adipokine levels were measured using a Milliplex™ MAP kit (Millipore).

Histological Analysis and Immunohistochemistry.

Tissues were fixed in 4% phosphate-buffered formalin, embedded in paraffin, sectioned at 4 µm, and stained with hematoxylin and eosin according to standard procedures. For immunohistochemistry, tissues were deparaffinized in xylene and rehydrated. Slides were incubated with 5% normal donkey serum in PBS (+0.2% Triton-X100 and 1% BSA) for 30 min, and subsequently sections were incubated overnight with a 1:200 dilution of primary antibodies at 4° C. and using Alexa Fluor 488 or 595 as secondary antibodies for 2 hrs at RT.

Metabolic Studies.

Glucose tolerance tests (GTT) were conducted after overnight fasting. Mice were injected intraperitoneally (i.p.) with 1 g of glucose per/kg body weight, and blood glucose was monitored at 0, 15, 30, 60, 90, and 120 min using a OneTouch Ultra glucometer (Lifescan Inc). Insulin tolerance tests (ITT) were conducted after overnight fasting. Mice were injected i.p. with 0.5 U of insulin/kg body weight (Humulin R; Eli Lilly), and blood glucose was monitored at 0, 15, 30, 60, 90, and 120 min using a OneTouch Ultra glucometer (Lifescan Inc). Real-time metabolic analyses were conducted in an undisturbed room under 12 h/12 h light/dark cycles using a Comprehensive Lab Animal Monitoring System (Columbus Instruments).

In Example 5, ob/ob male mice (8 wk old) were randomized into three groups and treated with daily subcutaneous (s.c.) injections of recombinant mouse FGF-1 (0.5 mg/kg in PBS), oral rosiglitazone (TZD, 5 mg/kg in 0.5% carboxymethyl cellulose), or vehicle. Blood glucose levels were measure in fed animals one hour after treatment. Total body composition analysis was performed using an EchoMRI-100™ (Echo Medical Systems, LLC).

Gene Expression Analysis.

Total RNA was isolated from mouse tissue and cells using TRIzol reagent (Invitrogen). cDNA was synthesized from 1 µg of DNase-treated total RNA using SuperScript II reverse transcriptase (Invitrogen). mRNA levels were quantified by QPCR with SYBR Green (Invitrogen). Samples were run in technical triplicates, and relative mRNA levels were calculated by using the standard curve methodology and normalized against 36B4 mRNA levels in the same samples.

Statistical Analysis.

All values are given as means±standard errors. The two-tailed unpaired Student's t-test was used to assess the significance of difference between two sets of data. Differences were considered to be statistically significant when P<0.05.

Example 1

Identification of FGF-1 as a Direct Target of PPARγ

To identify nuclear hormone receptor (NHR) targets, we used a "Promoter Ontology" screen, which encompasses a validated cDNA expression library including all 49 mouse NHRs combinatorially paired with a large collection of pathway specific promoter-reporter libraries. The pairing facilitates rapid evaluation of the transcriptional regulation of each genetic pathway by any NHR in a given context. Using this high-throughput promoter screen, we screened promoter constructs for members of the FGF family for regulation by the NHRs, and identified FGF-1 as a direct target of PPARγ. More specifically, we identified strong and specific transcriptional regulation of FGF-1 by PPARγ.

FGF-1A Promoter Characterization.

The expression of the FGF-1 gene is directed by at least three distinct promoters driving the untranslated exons: 1A, 1B, and 1D, spaced up to 70 kilobase pairs apart (FIG. 1A) (Myers et al., 1993). Alternative splicing of these untranslated exons to the three coding exons of the FGF-1 gene results in identical but differentially expressed FGF-1 polypeptides. In mice, FGF-1A shows the highest expression in heart and kidney but is also expressed in adipose and several other tissues (FIG. 1B). FGF-1B is the only variant expressed in brain, and is also expressed in several other tissues (FIG. 1C). FGF-1D is primarily expressed in liver (FIG. 1D).

Figure 2:
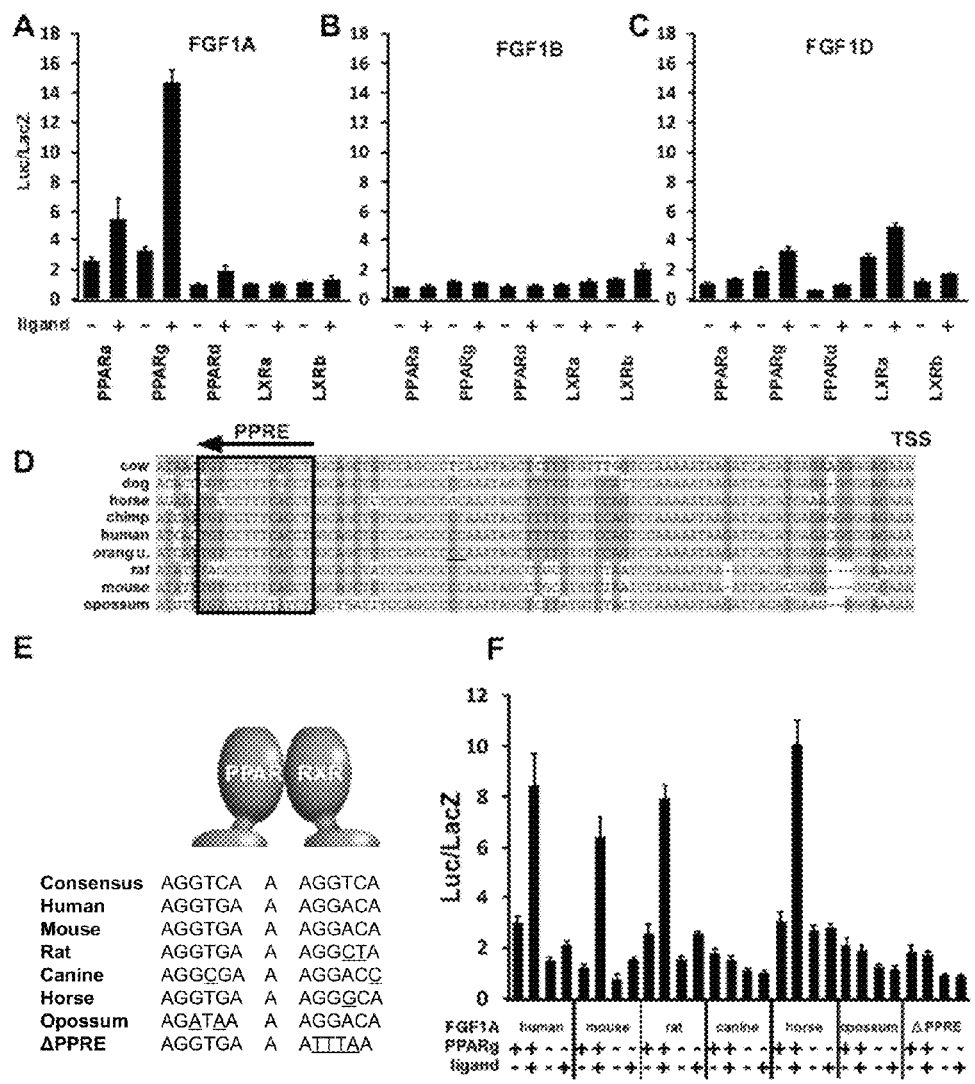
FIG. 2. FGF-1A is a direct transcriptional target of PPARγ. Determination of NR-mediated transcriptional regulation of (A) FGF-1A, (B) FGF-1B, and (C) FGF-1D using luciferase reporter assays. (D) Conserved PPAR response element (PPRE) within the proximal promoter of FGF-1A relative to the transcription start site (TSS). The sequences are shown from the indicated species, numbered SEQ ID NOs:1-9 from top to bottom. (E) Alignment of the PPRE within the FGF-1A promoter of different species. Underline indicates nucleotide variations between the PPREs relative to human. Sequence legend (top to bottom): SEQ ID NOs: 10-17. (F) Species-specific response of the FGF-1A promoter to PPARγ using luciferase reporter assays.

The transcriptional regulation of FGF-1 by PPARγ was mediated through binding of PPARγ to a PPAR response element (PPRE) located in one of the alternative promoters of FGF-1, named FGF-1A (FIG. 2A). Inactivation of the PPRE in the FGF-1A promoter (located at −60 bp relative to the transcription start site (TSS)) by site directed mutagenesis resulted in a complete loss of response of the FGF-1A promoter to PPARγ (FIG. 2F, compare human vs. ΔPPRE).

The gene structure of FGF-1 is highly conserved in a wide range of mammals (e.g., bovine, canine, horse, chimpanzee, orangutan, rat, mouse, and opossum). The PPRE in the FGF-1A promoter in these species also showed strong conservation (FIGS. 2D, E). To test the responsiveness of these PPREs to PPARγ, we changed the PPRE of the human FGF-1 promoter by site directed mutagenesis into the PPRE sequence of species that displayed sequence variation (rat, canine, horse, and opossum). PPARγ activation of the promoter was retained in all species except for the more distantly related canine and opossum (FIG. 2F). Together, these findings suggest a physiologically important function of regulation of the FGF-1A promoter by PPARγ, present in a wide range of mammals. In addition to a strong conservation of the PPRE in this promoter, several other highly conserved elements were detected (e.g., SP1, HMTB, EVI1, and E-box).

Figure 21:
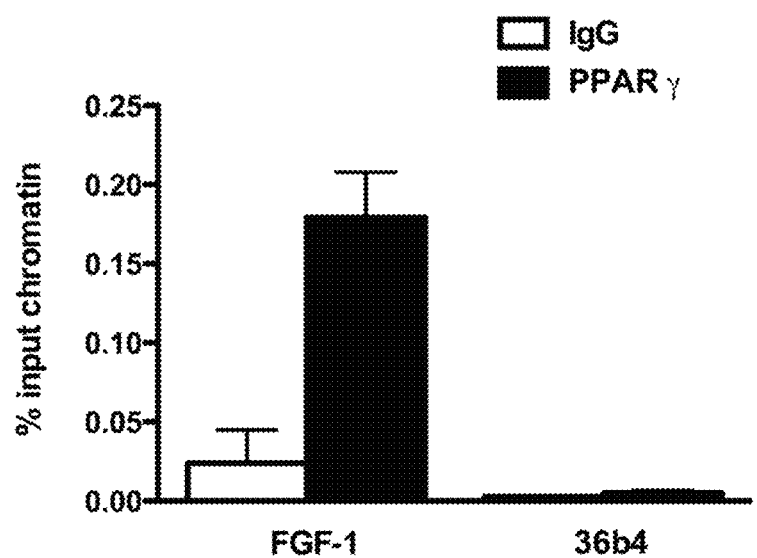
FIG. 21. PPARγ binds to the FGF-1 promoter region in mature adipocytes. Chromatin was prepared from differentiated 3T3-L1 adipocytes and chromatin immunoprecipitation assays were performed with either IgG antibodies (negative control) or anti-PPARγ antibodies. Quantitative PCR demonstrates that PPARγ specifically binds the FGF1 promoter region. 36b4 is a negative control locus devoid of PPARγ binding sites.

The role of PPARγ in FGF-1 expression was confirmed in mature adipose cells. FIG. 21 shows the results of quantitative PCR, demonstrating that PPARγ specifically binds the FGF1 promoter region. 36b4 is a negative control locus that does not include PPARγ binding sites.

FGF-1 is Regulated by PPARγ In Vivo.

Figure 3:
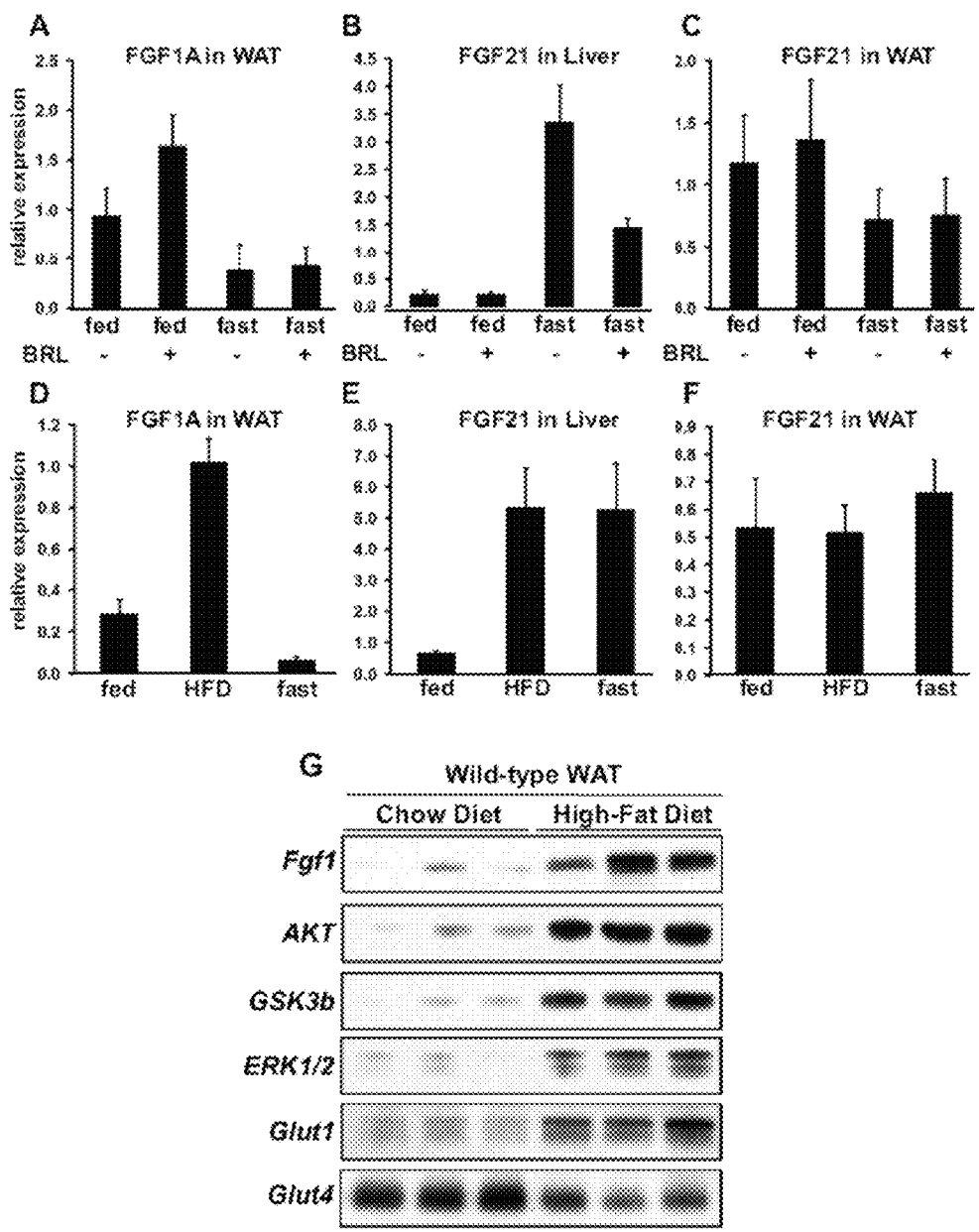
FIG. 3. Transcriptional regulation of FGF-1A in vivo. Levels of FGF-1A (A, D) and FGF21 (B, C, E, F) mRNA in WAT and liver of wild-type mice (n=5). (A, B, and C): Fed or overnight fast, with or without rosiglitazone (5 mg/kg for 3 days p.o.). (D, E, and F): Fed, 2 weeks HFD, or overnight fast. (G) Levels of FGF-1 protein and various components of the insulin signaling pathway in WAT of wild-type mice on a normal chow diet vs. 3 months HFD (n=3).

Short term oral administration of rosiglitazone (5 mg/kg for 3 days) or high-fat diet (two weeks) significantly increased the mRNA levels of FGF-1A in WAT (FIGS. 3A, D). This increase was similar to that of the adipocyte protein aP2 (also known as fatty acid binding protein 4, FABP4), which is the strongest known PPARγ target in adipose tissue. On the other hand, overnight fasting resulted in an about two-fold decrease in FGF-1A mRNA levels. For comparison, levels of FGF-21 were highly induced in the liver by fasting and HFD (FIGS. 3B, E) whereas no effects of rosiglitazone or HFD were observed in WAT (FIGS. 3C, F). Interestingly, rosiglitazone also reduced the expression of FGF-21 in fasted liver (FIG. 3B), which is also observed in patients with type 2 diabetes (Li et al., 2009). No changes in expression by TZD, HFD, or fasting were observed for FGF-1B and FGF-1D in liver, and for FGF-1B in WAT. FGF-1A and FGF-1D were not detected in liver and WAT, respectively. HFD treatment for 3 months in mice also resulted in increased protein levels of FGF-1 (FIG. 3G).

Example 2

FGF-1 Protects Against HFD-Induced Insulin Resistance

Figure 4:
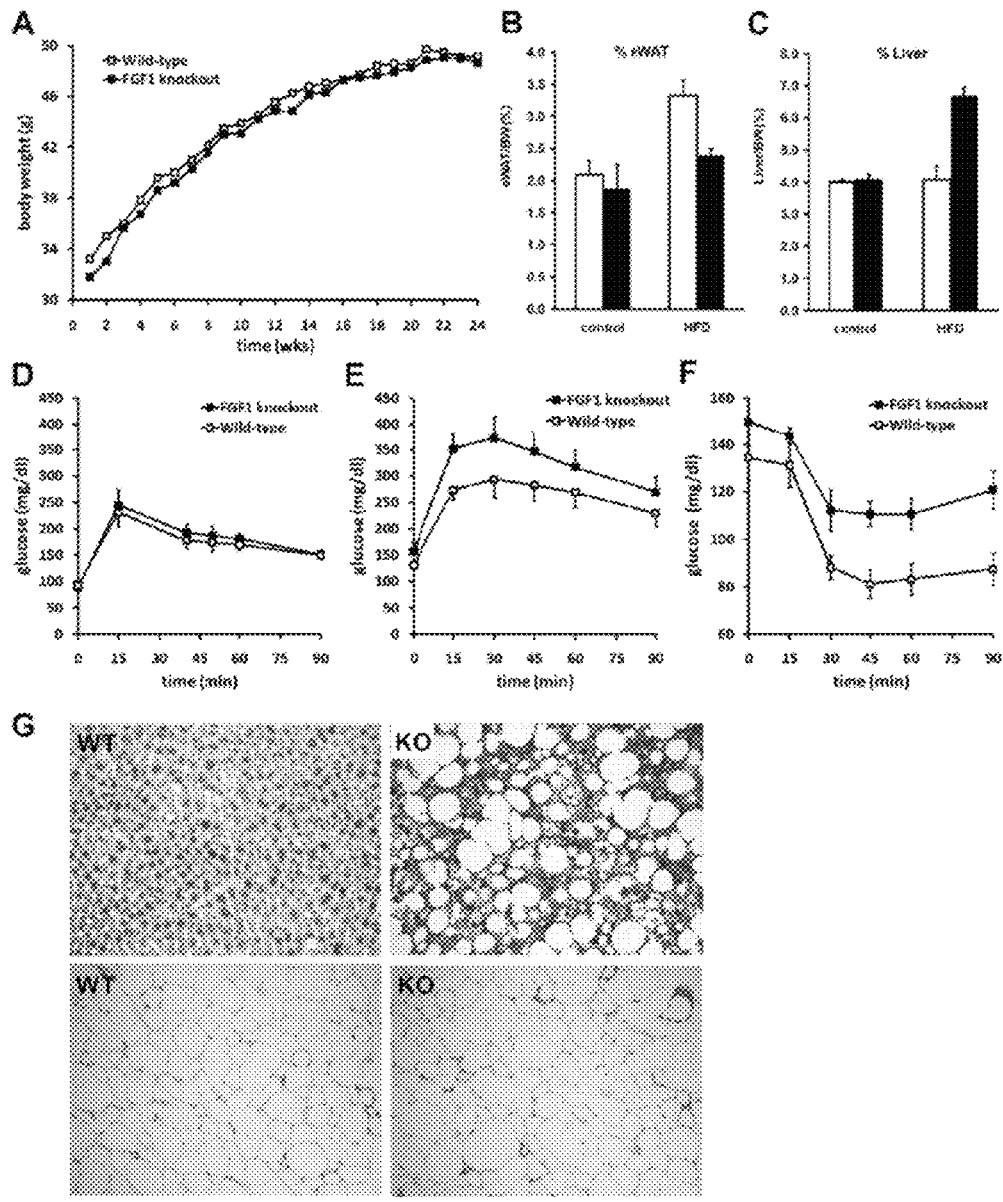
FIG. 4. HFD-induced insulin resistance in FGF-1 KO mice. In response to HFD diet, FGF-1 KO mice display (A) normal weight gain, (B) reduced epididymal white adipose (eWAT) weight gain, and (C) increased liver weight as compared to wild-type littermates (n=6-7). FGF-1 KO mice display (D) normal glucose tolerance when fed with control diet, but develop HFD-induced insulin resistance as indicated by (E) decreased glucose tolerance and (F) increased insulin tolerance after 6 mo HFD. (G) histology (H&E) of liver (upper panels) and WAT (lower panels) of wild-type (left panels) and FGF-1 KO (right panels) animals. Histological analysis of 6-month HFD-treated FGF-1 knockout and wild-type mice. FGF-1 KO mice display (H) normal pancreatic islet morphology and organization, (I) increased hepatic steatosis, and (J) normal adipocyte size and morphology.
Figure 4:
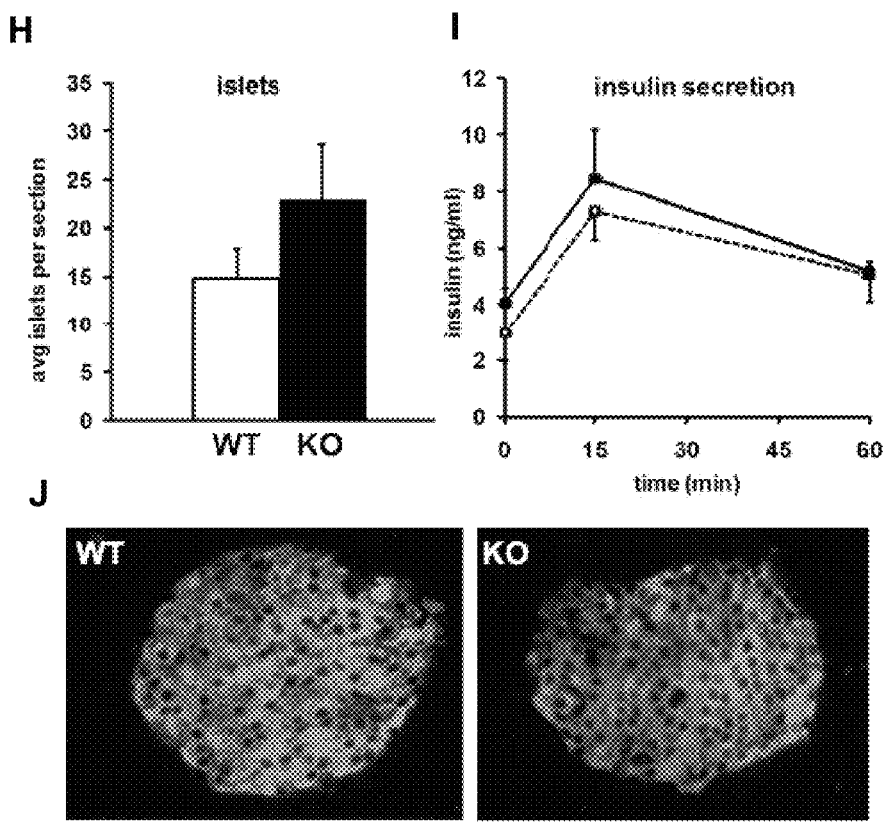

Next, we determined the consequences of loss of FGF-1 in vivo, using FGF-1 knockout (KO) mice. FGF-1 KO mice have been studied in the context of wound healing and cardiovascular changes. Neither these mice, nor FGF-1/FGF2 double KO mice, displayed any significant phenotype under normal feeding conditions (Miller et al., 2000). To study the role of PPARγ-mediated regulation of FGF-1, FGF-1 KO and wild-type littermates were fed a high fat diet (HFD). Although no difference in HFD-induced weight gain was observed (FIG. 4A), FGF-1 KO mice had smaller WAT and larger, steatotic livers, suggesting that FGF-1 KO mice fail to increase their adipose mass and alternatively mobilize fat into the liver (FIGS. 4B, C). At the same time, FGF-1 KO mice displayed increased fasting levels of glucose and insulin and increased insulin resistance compared to wild-type littermates as demonstrated by glucose- and insulin-tolerance tests (GTT, ITT), respectively (Tables 1 and 2, FIGS. 4 D-F). No obvious abnormalities were observed in pancreas function as indicated by normal islet morphology, histology, and glucose-stimulated insulin secretion. The number of islets per pancreas, however, was slightly increased (FIG. 4H).

TABLE 1

Metabolic parameters of male wild-type and FGF-1$^{-/-}$ mice after 3 months high fat diet feeding.

|  | wild-type | FGF-1$^{-/-}$ |  |
| --- | --- | --- | --- |
| Insulin | 0.32 ± 0.12 | 0.50 ± 0.34 | ng/ml |
| Glucose | 103 ± 21 | 119 ± 24 | mg/dl |
| Leptin | 6.3 ± 2.0 | 6.7 ± 1.2 | ng/ml |
| Resistin | 5.4 ± 1.4 | 5.6 ± 1.4 | ng/ml |
| IL-6 | 12.4 ± 3.6 | 13.9 ± 11.0 | pg/ml |
| TNFα | 8.7 ± 1.2 | 8.1 ± 0.7 | pg/ml |
| MCP-1 | 48.0 ± 3.4 | 59.0 ± 3.4** | pg/ml |
| tPAI-1 | 0.58 ± 0.68 | 0.33 ± 0.33 | ng/ml |
| Body weight | 39.9 ± 2.8 | 40.9 ± 2.8 | g |

Results are expressed as mean serum concentrations after an overnight fast±SD, n=6; nd, *P<0.05.

TABLE 2

Metabolic parameters of male wild-type and FGF-1$^{-/-}$ mice after 5 months high fat diet feeding.

|  | wild-type | FGF-1$^{-/-}$ |  |
| --- | --- | --- | --- |
| Insulin (fast) | 2.7 ± 0.9 | 3.7 ± 0.4* | ng/ml |
| Glucose (fast) | 159 ± 17 | 183 ± 29* | mg/dl |
| Adiponectin (fast) | 12.9 ± 1.2 | 13.7 ± 1.8 | µg/ml |
| Total cholesterol (fed) | 46.6 ± 12.3 | 44.6 ± 6.6 | mg/dl |
| Total cholesterol (fast) | 49.2 ± 17.5 | 50.4 ± 3.1 | mg/dl |
| Free Fatty Acids (fed) | 0.13 ± 0.02 | 0.11 ± 0.04 | ng/ml |
| Free Fatty Acids (fast) | 0.20 ± 0.01 | 0.19 ± 0.02 | ng/ml |
| Triglycerides (fed) | 16.88 ± 2.3 | 16.1 ± 1.9 | mg/dl |
| Triglycerides (fast) | 11.2 ± 1.5 | 10.2 ± 0.9 | mg/dl |
| Body weight (BW) | 46 ± 2.4 | 47 ± 1.2 | g |
| Liver weight | 1.9 ± 0.3 | 2.4 ± 0.3* | g |
| Liver % | 4.1 ± 0.5 | 5.1 ± 0.5* | % BW |
| WAT weight | 1.9 ± 0.3 | 1.3 ± 0.1* | g |
| WAT % | 4.4 ± 0.9 | 2.8 ± 0.2* | % BW |
| Kidney weight | 486 ± 30 | 463 ± 45 | mg |
| Heart weight | 209 ± 12 | 196 ± 9 | mg |

Results are expressed as mean serum concentrations or weights±SD, n=5; nd, *P<0.05.

Example 3

AKT Signaling is Impaired in WAT of HFD-Fed FGF-1 KO Mice

Figure 5:
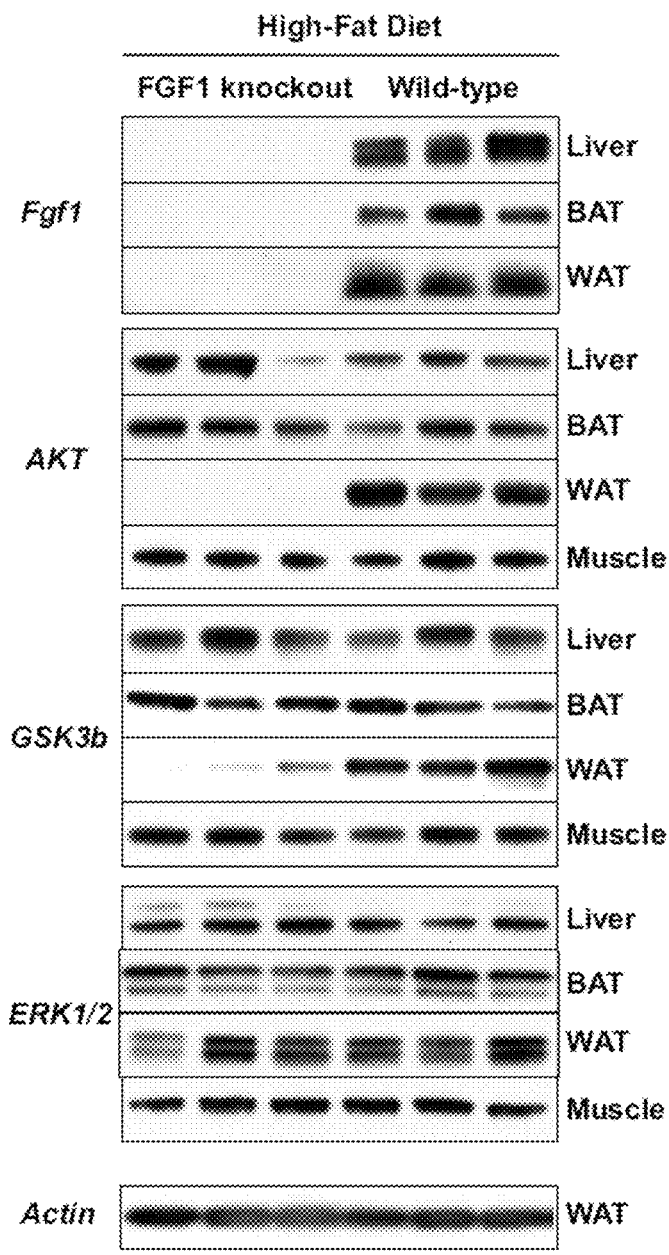
FIG. 5. HFD-induced loss of AKT signaling in WAT of FGF-1 KO mice. Protein levels of FGF-1, AKT, GSK3b, ERK1/2, and actin in liver, BAT, WAT, and muscle of HFD-treated (6 months) FGF-1 KO and wild-type mice (n=3). FGF-1 was not detected in muscle.

FGFs signal through four cognate high-affinity tyrosine kinase receptors, designated FGFR-1 to −4, leading to downstream activation of multiple signal transduction pathways, including the MAPK (ERK1/2) and PI3K/AKT pathways. These pathways regulate components of the insulin/glucose signaling pathways including activation of glycogen synthase kinase-3 (GSK-3), which regulates glycogen synthesis in response to insulin, and translocation of the glucose transporter GLUT4 (Cho et al., 2001). To investigate the integrity of these signaling pathways, we determined the expression of its critical components in WAT, BAT, liver, and muscle of HFD-fed FGF-1 KO and wild-type mice (FIG. 5). Interestingly, we found that total levels of AKT (and to a lesser extent GSK3β) were reduced in WAT of HFD-treated FGF-1 KO mice compared to WT mice. In contrast, levels of AKT were normal in liver, BAT, or muscle, and levels of ERK1/2 were normal in all four tissues.

Example 4

FGF-1 Induces GLUT1 In Vitro

Figure 6:
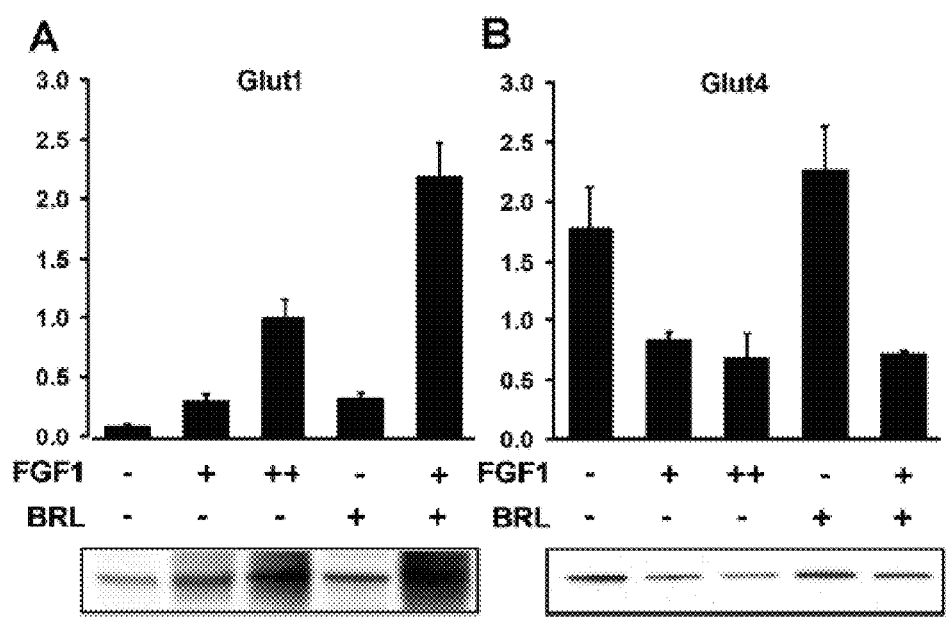
FIG. 6. FGF-1 and rosiglitazone stimulation of Glut1 expression in 3T3-L1 adipocytes. 3T3-L1 adipocytes were treated with FGF-1 (+=50 ng/ml, ++=100 ng/ml), rosiglitazone (1 µM), or in combination. (A) mRNA (top) and protein (bottom) levels of Glucose Transporter 1 (Glut1); (B) mRNA (top) and protein (bottom) levels of Glucose Transporter 4 (Glut4).

FGF-1 induces the expression of GLUT1 and acts synergistically with rosiglitazone in 3T3-L1 adipocytes. FGF-1 induces the expression of Glucose Transporter 1 (Glut1) in mouse 3T3-L1 adipocytes after prolonged treatment (FIG. 6), and it decreases fed blood glucose in ob/ob mice. The results indicate that FGF-1 can be used as a therapy for treating diabetes and obesity.

Example 5

FGF-1 has Hypoglycemic Effects In Vivo

Figure 7:
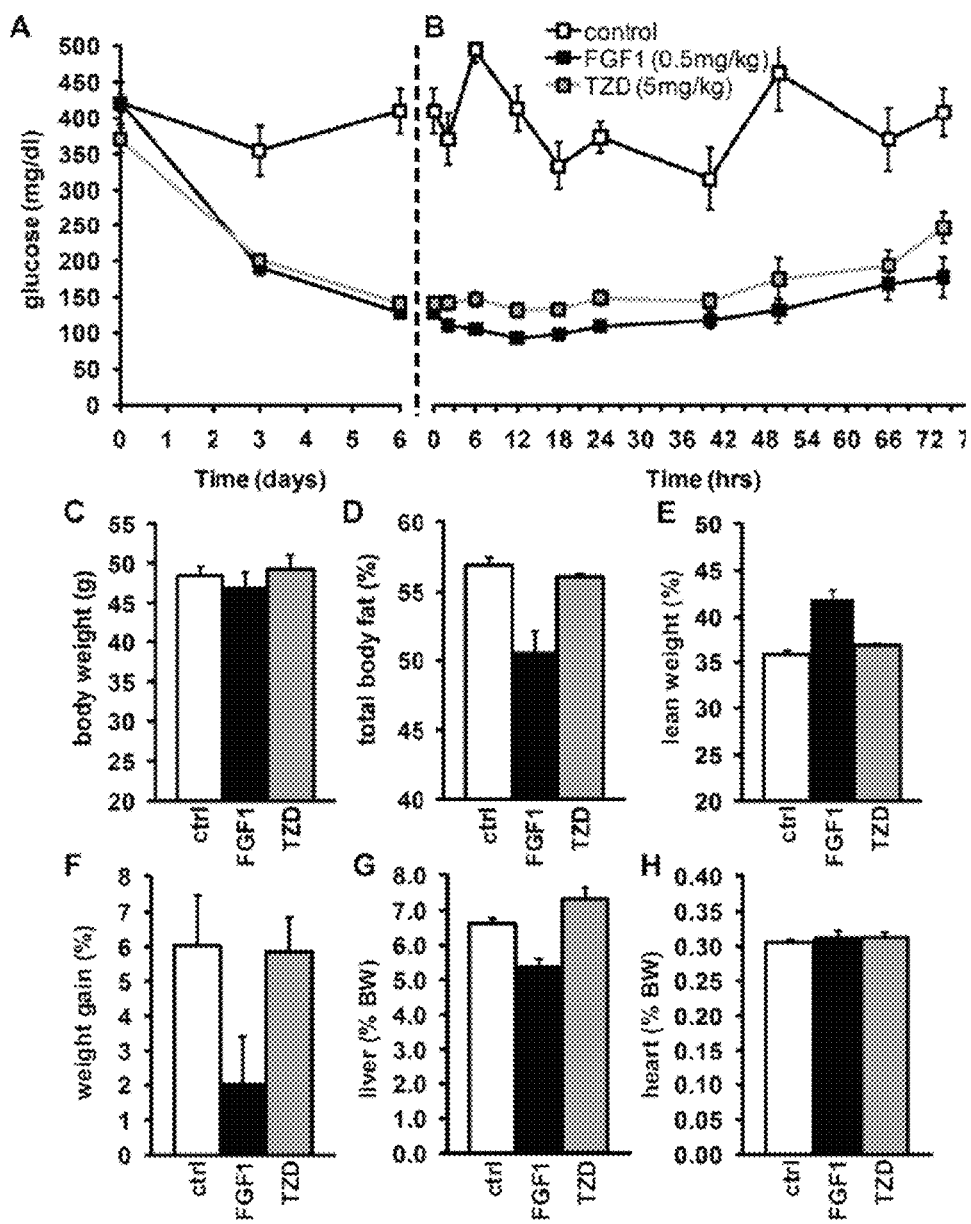
FIG. 7. FGF-1 injection studies in rodents. (A) Fed blood glucose in ob/ob male mice treated with FGF-1 (0.5 mg/kg, s.c.), rosiglitazone (TZD, 5 mg/kg, p.o.), or vehicle. FGF-1 was administered once daily, and blood glucose levels were measured at day 0 (basal levels before FGF-1 injection), day 3, and day 6, 1 hour after injection. The values (±SE) shown are the average of the measurements of 5 animals in a group; (B) Sustained glucose lowering effects of FGF-1: Fed blood glucose levels in ob/ob mice at indicated time points after the last FGF-1 injection at day 6. (C—H): 72 hrs after the sixth dose, another dose was given and effects of FGF-1 and TZD on (C) body weight, (D) total body fat, (E) lean weight, (F) weight gain, (G) liver weight, and (H) heart weight were determined.

Eight-week-old male ob/ob mice were treated with recombinant mouse FGF-1 (0.5 mg/kg/day, s.c. in 250 µL1), rosiglitazone (TZD, 5 mg/kg/day, p.o. in 300 µL1), or vehicle control (s.c. vehicle control 0.9% NaCl, 250 µl/mouse; p.o. vehicle control 0.5% CMC, 300 µl/mouse). Blood glucose was measured one hour after treatment at day 3 and day 6 using a standard protocol. (FIG. 7A).

Before treatment, all groups were severely hyperglycemic, as indicated by blood glucose levels of about 400 mg/dl. At day three, both FGF-1-treated and TZD-treated groups exhibited greatly reduced blood glucose levels, about 200 mg/dl. At 6 days, blood glucose levels were even further reduced to around 130-140 mg/dl for both groups. After the sixth dose, blood glucose levels were monitored for another 72 hrs. During this period, both FGF-1- and TZD-treated cohorts maintained normoglycemic levels (<140 mg/dl) for at least 48 hrs (FIG. 7B). At 72 hrs after the sixth dose, a final dose was given, and 12 hrs later, a total body composition analysis was performed by MRI followed by necropsy.

The results show that FGF-1 is selectively induced in adipose tissue by high-fat diet (HFD) and TZD, and mice lacking FGF-1 develop HFD-induced insulin resistance (IR). At the molecular level, the IR of these mice can be explained by impaired AKT signaling in adipose. Administration of FGF-1 to diabetic mice normalizes their glucose levels and improves their fat-lean ratio. Thus, FGF-1 acts as a powerful insulin sensitizer in adipose tissue and mediates insulin sensitizing actions of TZDs and PPARγ.

Example 6

FGF-1 Rapidly and Dramatically Reduces Glucose Levels in Ob/Ob Diabetic Mice

Figure 8:
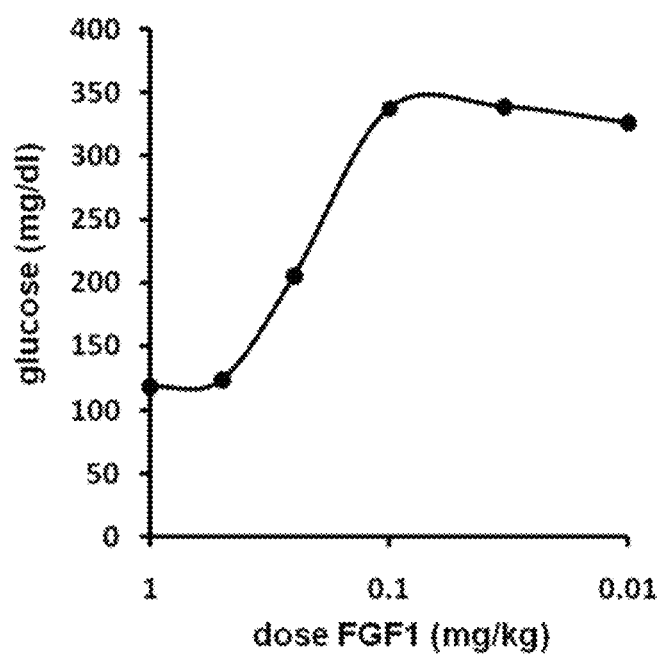
FIG. 8. Dose response effect of FGF-1 (s.c., mg/kg) on blood glucose levels of ob/ob mice. The maximum glucose lowering effects of FGF-1 are reached at 0.5 mg/kg with an EC50=0.25 mg/kg.
Figure 9:
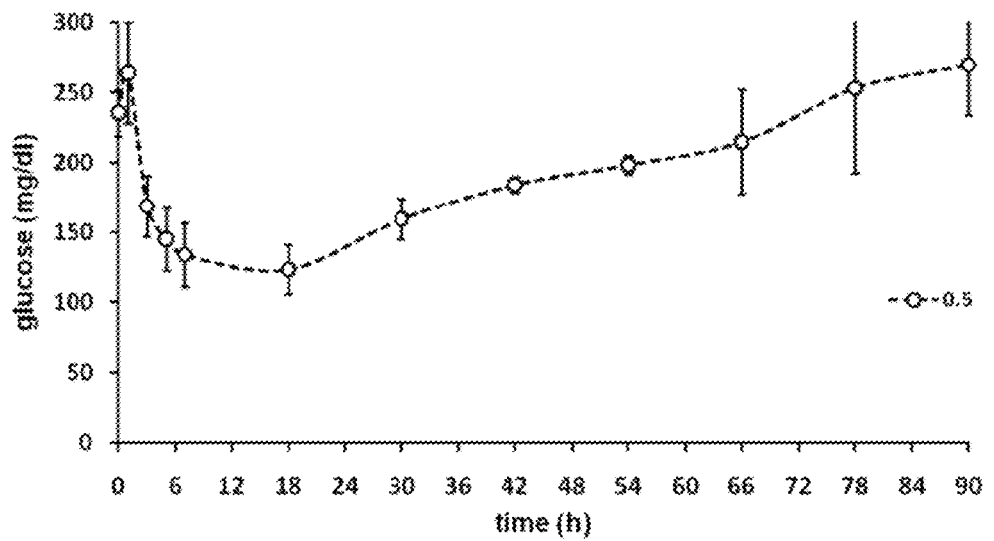
FIG. 9. Effect of FGF-1 (s.c., 0.5 mg/kg) on blood glucose levels of ob/ob mice. The results show that a single s.c. dose reduces blood glucose for more than 2 days.
Figure 10:
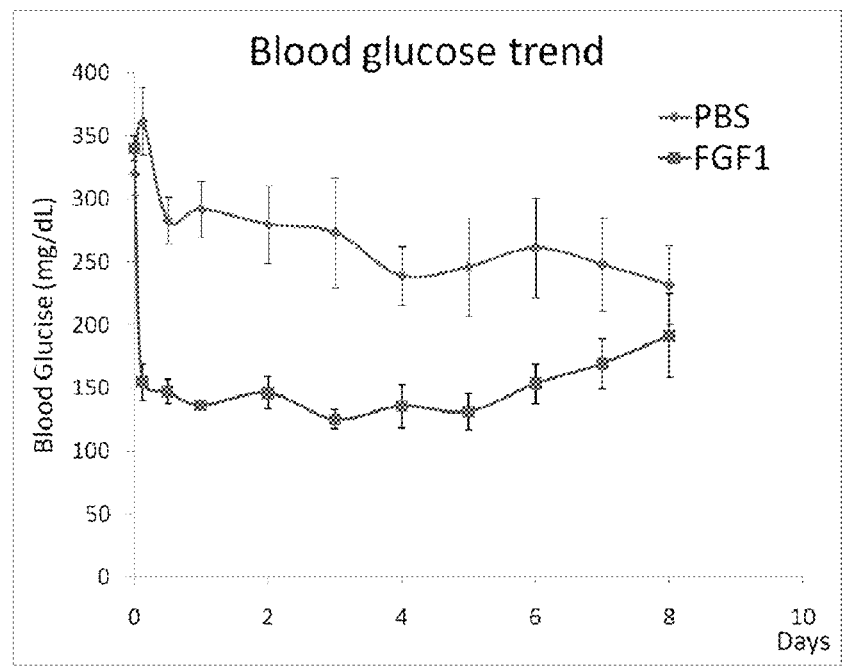
FIG. 10. Effect of intravenous FGF1 (0.2 mg/kg) on blood glucose levels of ob/ob mice. IV administration of FGF1 has acute glucose lowering effects, which last up to one week.

In order to establish the acute effects of FGF-1 on blood glucose levels, dose response curves (FIG. 8) and time courses after subcutaneous (FIG. 9) and intravenous (FIG. 10) administration were performed. The results show that FGF-1 causes dramatic dose-dependent reduction of glucose levels in ob/ob mice. Subcutaneous dosing is effective within a matter of hours, and the significant reduction in glucose levels lasts at least 2 days (FIG. 9). FIG. 10 shows that intravenous administration results in an even longer lasting effect on glucose levels, so that a dose of 0.2 mg/kg body weight resulted in significantly reduced blood glucose for at least one week.

Example 7

Chronic Administration of FGF-1 Results in Normalized Blood Glucose Levels

Figure 11:
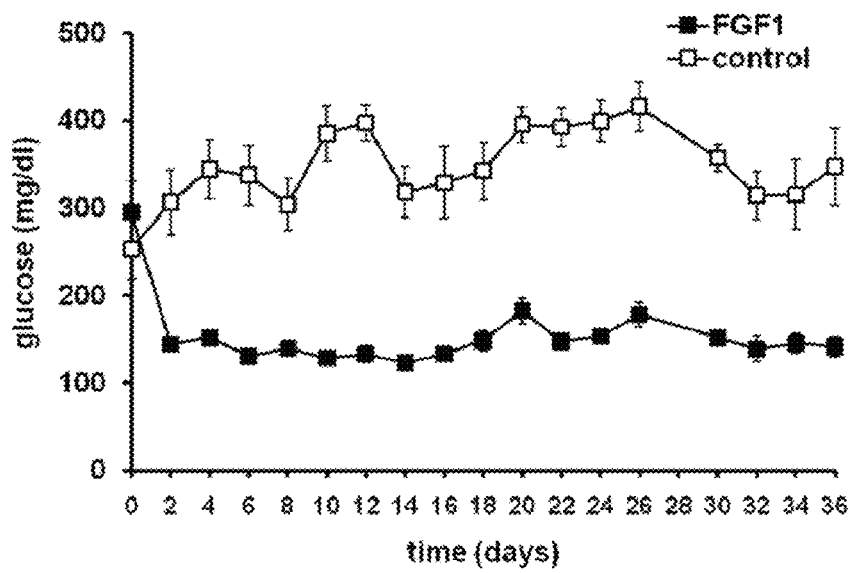
FIG. 11. Effect of chronic FGF-1 on blood glucose. FGF-1 treatment every third day results in completely normalized blood glucose in ob/ob mice.

To investigate the metabolic effects of chronic FGF-1 treatment in ob/ob mice, eight weeks old male ob/ob mice were treated with vehicle or recombinant mouse FGF-1 (0.5 mg/kg/3 days, s.c.) for a period of 36 days. During this time, glucose levels, food intake, and body composition were monitored. FIG. 11 shows that glucose levels are normalized by the first time point tested (day 2) and remain stable for the remainder of the test period.

Example 8

Administration of FGF-1 Results in Reduced Body Weight and Percent Body Fat

Figure 12:
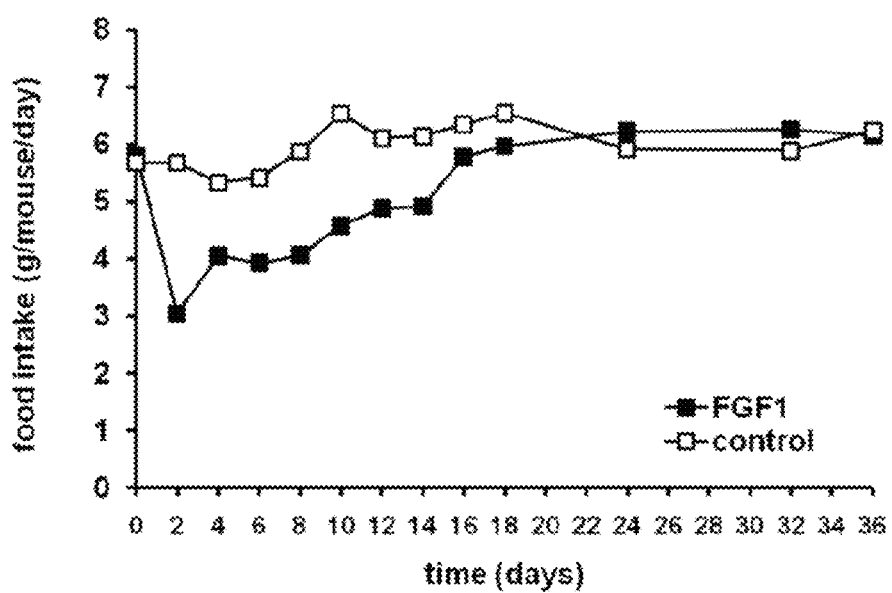
FIG. 12. Effect of chronic FGF1 on food intake. FGF-1 induces a reduced food intake during the first 1-2 weeks of chronic administration, but after two weeks food intake returned to normal.
Figure 13:
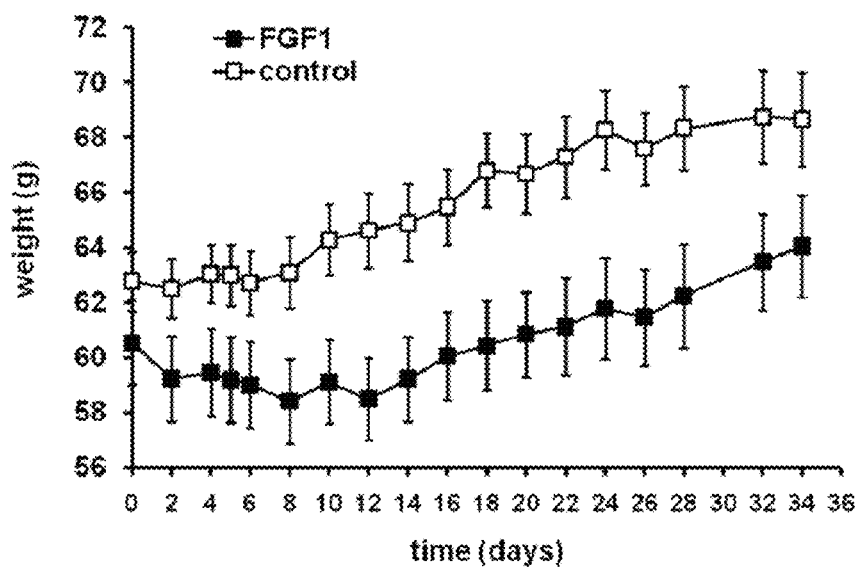
FIG. 13. Effect of chronic FGF-1 on body weight. FGF-1 treatment resulted in a reduced weight gain during the first week of chronic FGF1 administration. After one week, weight gain is similar between control and FGF1-treated mice. This reduced weight gain corresponds with reduced food intake, but is more durable. Reduced weight gain is evident after food intake returns to normal.

FIG. 12 shows that FGF-1 administration initially results in reduced food intake of ob/ob mice. Food intake returns to normal within about 2 weeks, but as shown in FIG. 13, body weight in FGF-1 treated ob/ob mice remains lower than in untreated ob/ob mice. The reduction in body weight shown in FIG. 13 indicates that FGF-1 can be used to produce rapid and durable body weight reduction.

Figure 14:
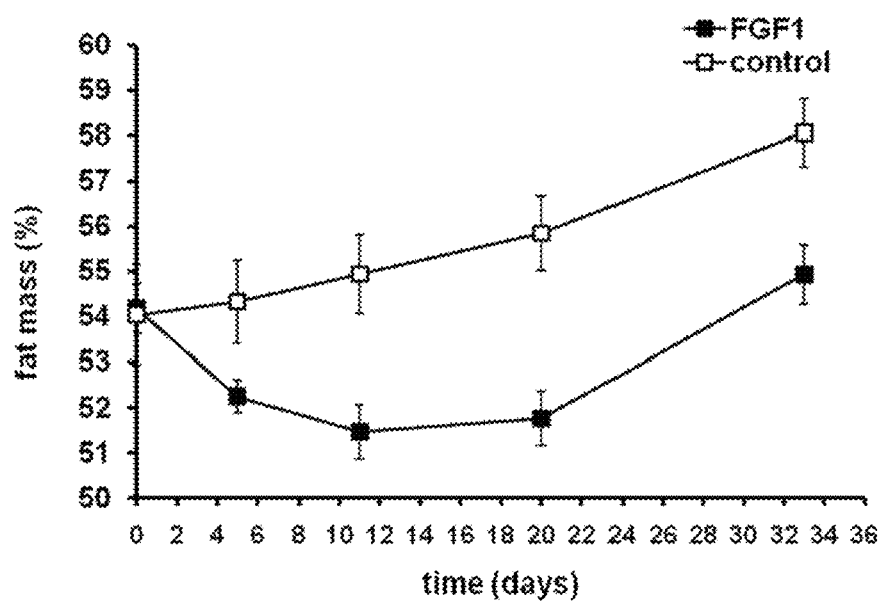
FIG. 14. Effect of chronic FGF-1 on total percent body fat. FGF-1 treated mice display reduced increase in percent body fat.
Figure 15:
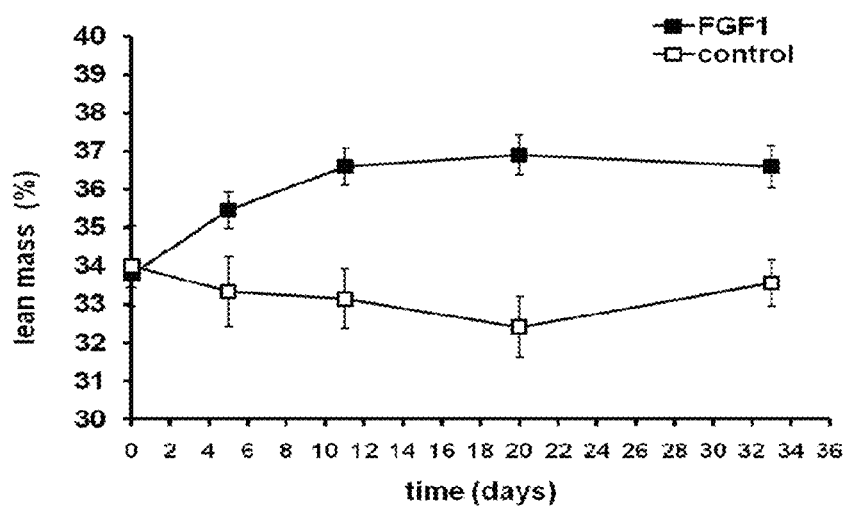
FIG. 15. Effect of chronic FGF-1 on percent lean mass. FGF-1 treated mice display increased lean mass as compared with control mice, further indicating that the reduced weight is due to a decrease in the percent body fat.

FIGS. 14 and 15 compare percent body fat and percent lean mass in FGF-1 treated and untreated ob/ob mice. The results indicate that the reduction in body weight is largely due to reduced percentage body fat. The relative percentage of lean mass in FGF-1 treated mice is significantly higher than in untreated mice (FIG. 15).

Example 9

FGF-1 Results in Improved Glucose Tolerance and Reduced Insulin Resistance

Figure 16:
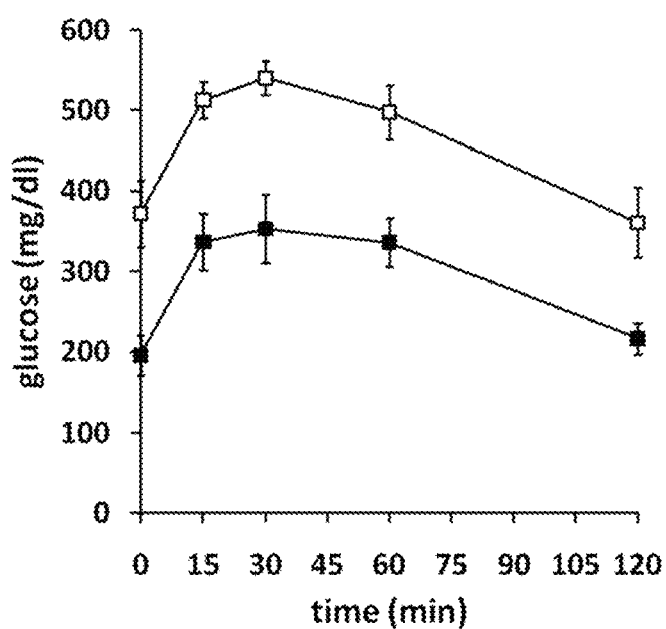
FIG. 16. Effect of chronic FGF-1 on glucose tolerance. Untreated mice show impaired glucose tolerance. After 4 weeks of FGF-1 administration, ob/ob mice display a more rapid and effective capacity to clear glucose from the blood, indicating that FGF-1 enhances glucose tolerance.
Figure 17:
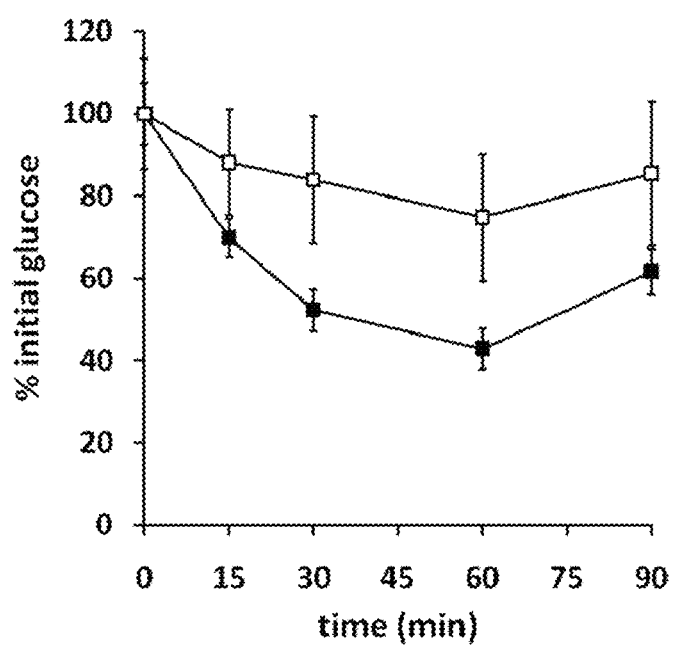
FIG. 17. Effect of chronic FGF-1 on insulin tolerance. After 4 weeks of chronic FGF-1 administration, ob/ob mice display increased insulin sensitivity. FGF-1 treated mice clear glucose from the blood more effectively than untreated mice.
Figure 18:
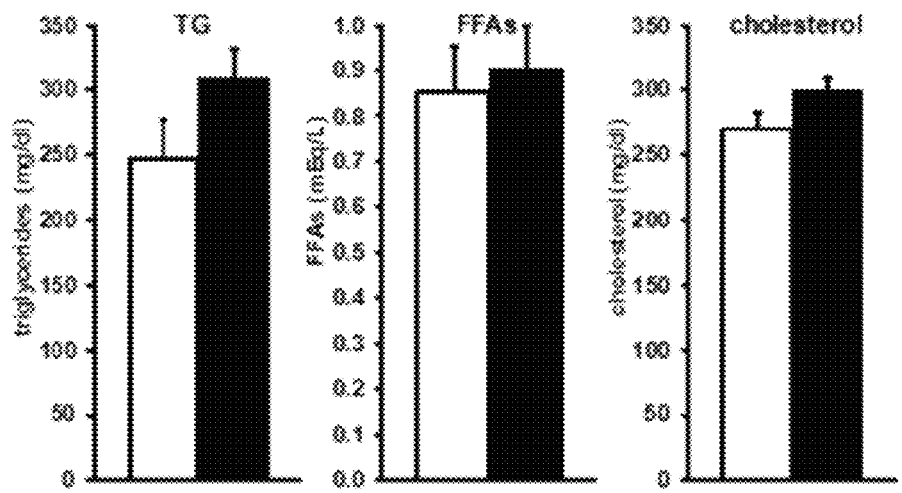
FIG. 18. Effect of chronic FGF-1 on serum lipids. Serum levels of triglycerides, free fatty acids, and cholesterol are similar between control and FGF-1 treated mice.

FIG. 16 shows the results of a glucose tolerance test carried out after four weeks of FGF-1 administration (0.5 mg/kg/3 days, s.c.). FGF-1 treated ob/ob mice cleared glucose more effectively than untreated controls. FGF-1 treated mice also showed increased insulin sensitivity, as indicated by more rapid clearance of glucose in the ITT (FIG. 17). Serum lipid levels (triglycerides, free fatty acids, and cholesterol) were similar between the two groups (FIG. 18). These tests were carried out as described above.

Example 10

FGF-1 Reduces Fatty Liver in Ob/Ob Mice

Figure 19:
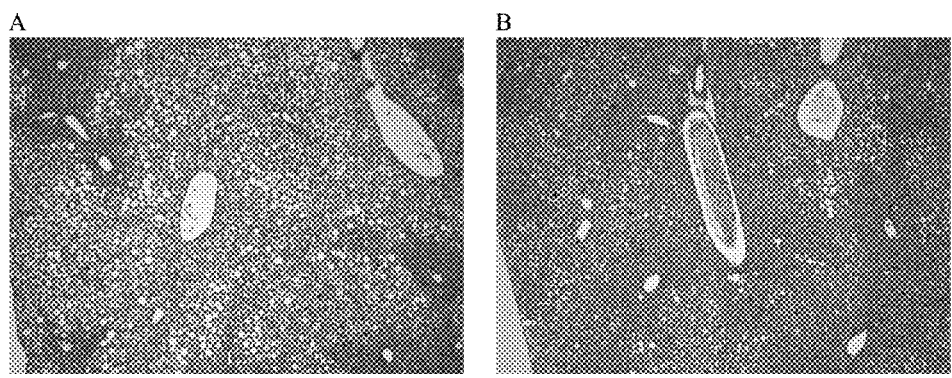
FIG. 19. Effect of chronic FGF-1 on hepatic steatosis. H&E staining of liver of A) control and B) FGF1-treated ob/ob mice. Control mice show mixed micro and macro vesicular steatosis with some periportal sparing. Steatosis affects most hepatocyes (>70%). There is little if any inflammatory infiltrate in either the portal tracts or lobules, which is typical liver histology for an ob/ob mouse. In contrast, livers from FGF-1 treated mice display clearing of fat in a periportal to mid zonal distribution. Steatosis is dramatically reduced compared to control and is mainly microvesicular. There is very little macrovesicular steatosis, and little or no inflammation.

Analysis of liver tissue after the 36 day treatment period revealed that the livers of FGF-1 treated ob/ob mice were much healthier than their untreated counterparts. FIG. 19 shows H&E stained tissue from untreated (A) and treated (B) mice. The untreated liver displays significant steatosis (fat deposit and damage), while the liver from FGF-1 treated mice shows much less steatosis, and little if any inflammation.

Figure 20:
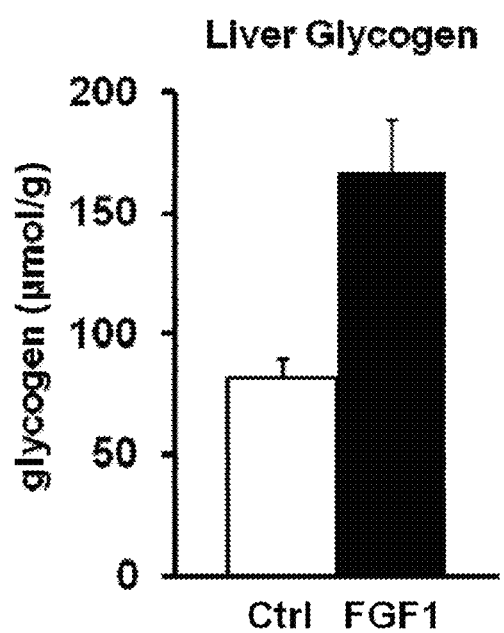
FIG. 20. Effect of chronic FGF-1 on hepatic glycogen. FGF-1 treated ice display increased levels of hepatic glycogen as compared to control mice.

Moreover, liver glycogen levels were much higher in FGF-1 treated mice, which is indicative of proper glucose processing and insulin response (FIG. 20).

Example 11

Multiple Delivery Methods of FGF-1 are Effective for Reducing Blood Glucose

Figure 22:
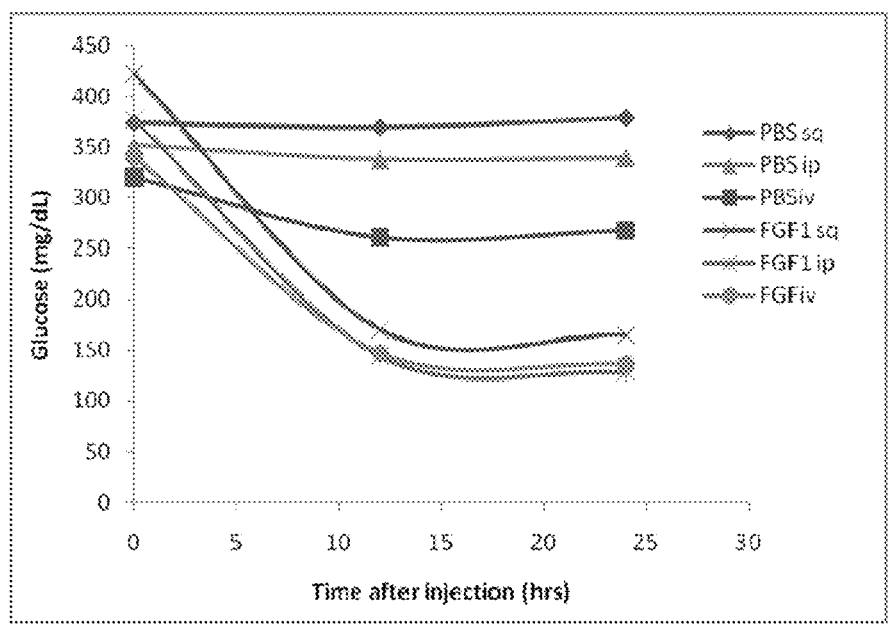
FIG. 22. Assessment of delivery method on FGF-1 blood glucose effects. Subcutaenous, intraperitoneal, and intravenous delivery of FGF-1 (0.5 mg/kg) display similar efficacy in normalizing blood glucose levels of ob/ob diabetic mice.
Figure 23:
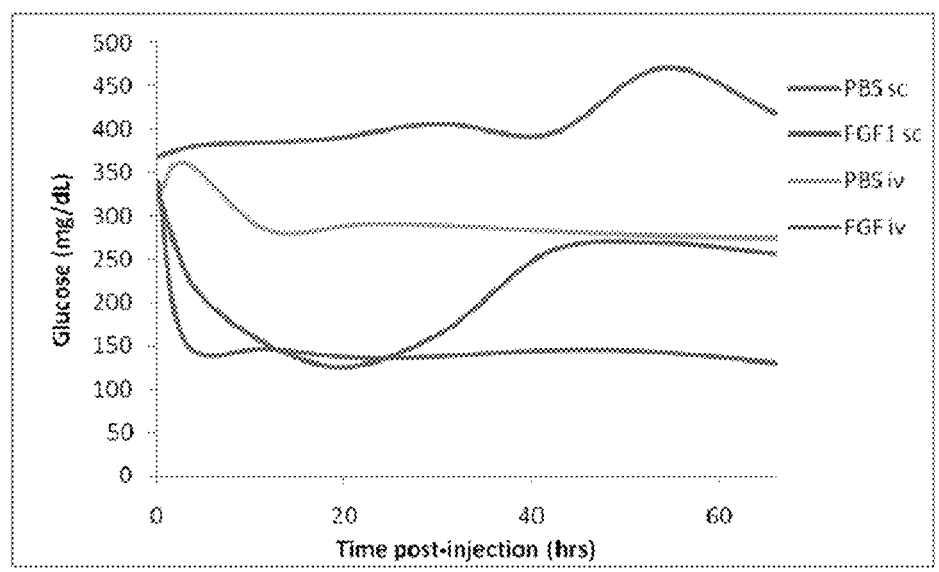
FIG. 23. Assessment of delivery method on duration of FGF-1 activity. Single subcutaneous (sc) or intravenous (iv) injection of FGF-1 (0.5 mg/kg) in ob/ob mice. FGF-1 glucose normalizing effects persist longer when administered iv as compared to sc.

To determine if the effects of FGF-1 depend on the route of administration, we tested blood glucose levels of ob/ob mice in response to 0.5 mg/kg body weight FGF-1 delivered s.c., i.p. and i.v. PBS injections were used as controls. FIG. 22 shows that the acute effects of FGF-1 are about the same for all three injection methods. We next compared i.v. and s.c. injections for duration of the glucose normalizing effect. As shown in FIG. 23, FGF-1 administered intravenously resulted in stable glucose levels for the duration of the test, at least 60 hours. The data from FIG. 10 indicate that the effects of intravenous injection are indeed much longer lasting (at least one week).

Example 12

FGF-1 is Effective for Normalizing Glucose in Other Diabetic Models

Figure 24:
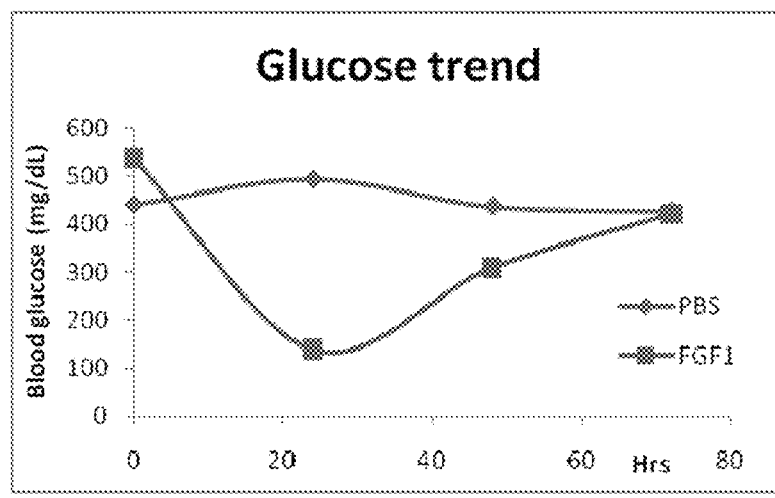
FIG. 24. FGF-1 effects in db/db mice. Single subcutaneous injection of FGF-1 (0.5 mg/kg) normalizes blood glucose in db/db leptin receptor mutant diabetic mice. The db/db model is considered to represent a less severe diabetes model than ob/ob. The results indicate that FGF-1 is effective for treatment of less severe metabolic disorders.
Figure 25:
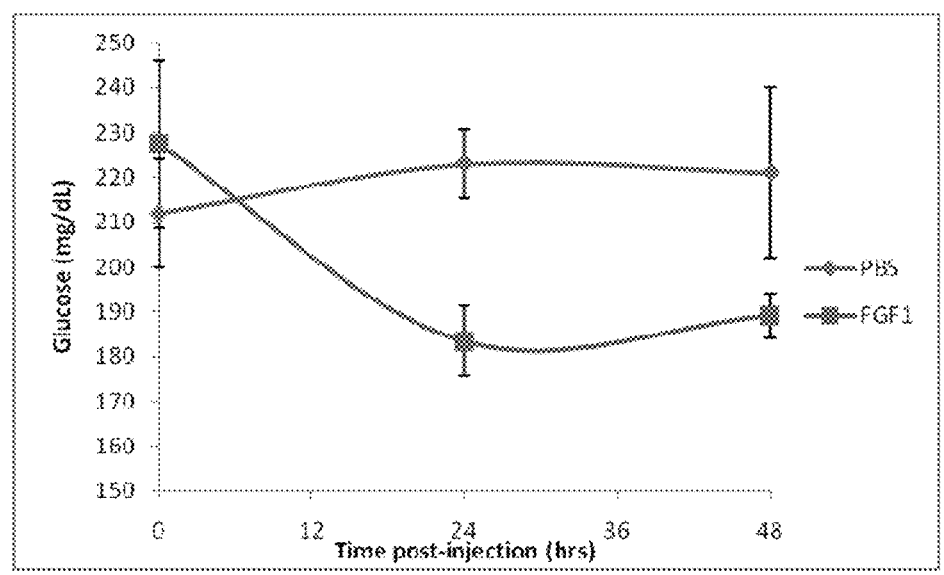
FIG. 25. FGF1 effects in DIO mice. Single subcutaneous injection of FGF1 (0.5 mg/kg) normalizes blood glucose in diet-induced obesity mice (C57BL/6). Again, the results indicate that FGF-1 is effective for treatment of metabolic disorders arising from a number of causes.

The ob/ob model is considered to represent a very severe diabetic disease. In order to investigate the effect of FGF-1 on less severe diabetic/metabolic disorder models, we tested blood glucose levels in db/db mice and diet induced obese mice. FIGS. 24 and 25 show that subcutaneous administration of 0.5 mg/kg FGF-1 was effective for reducing blood glucose levels in both systems. The data indicate that FGF-1 can be used to normalize glucose levels and treat metabolic disorders arising from different causes.

Example 13

Human Recombinant FGF-1 Effectively Reduces Glucose Levels in Ob/Ob Mice

Figure 26:
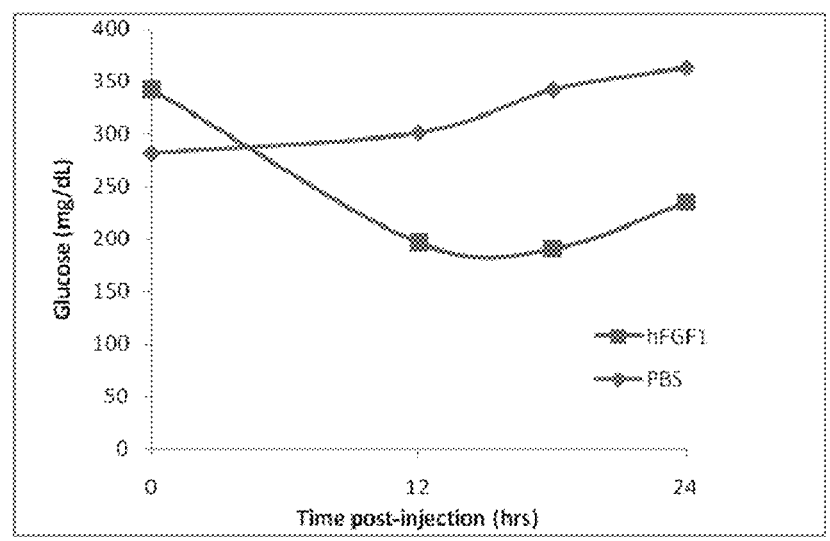
FIG. 26. Human recombinant FGF-1 is effective in mice. Single subcutaneous injection of human FGF1 (0.5 mg/kg) normalizes blood glucose in ob/ob mice.

FIG. 26 shows that the same dose of hrFGF-1 administered s.c. can effectively reduce glucose levels in ob/ob mice. As human recombinant FGF-1 is already being used in the clinic, the present methods of using it to treat metabolic disorders offer a straightforward regulatory path to treatment.

Example 14

Glucose Reducing Effects are Specific to FGF-1

Figure 27:
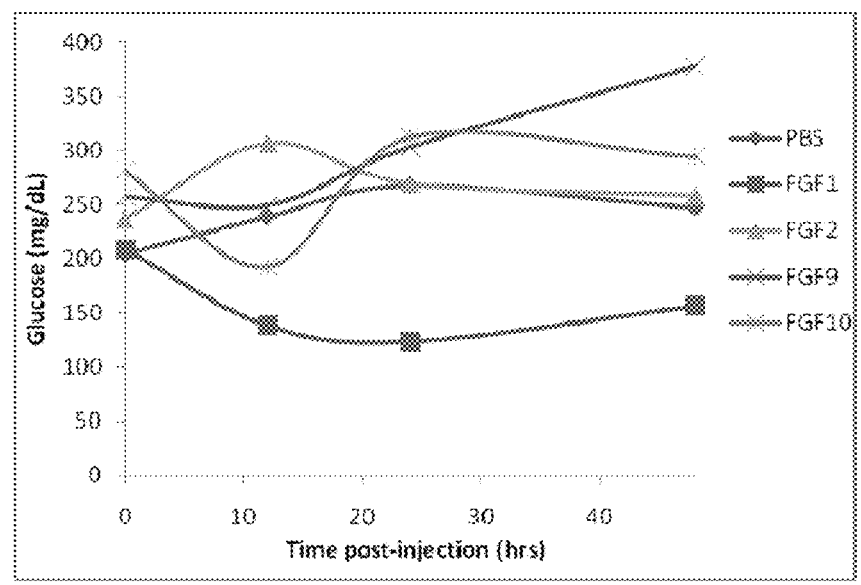
FIG. 27. Comparison of FGF1, FGF2, FGF9, and FGF10 effects. Single subcutaneous injection of FGFs (0.5 mg/kg) in ob/ob mice. Only FGF1 has glucose normalizing effects.

As explained above, the FGF family of factors bind to members of the FGFR family of receptors with different specificities. FGF-1 binds preferentially to FGFR1 and FGFR4, and can be internalized into a cell expressing these receptors. To determine if other FGF proteins have similar metabolic effects as FGF-1, we tested blood glucose in ob/ob mice treated with FGF-2, FGF-9, and FGF-10 (0.5 mg/kg s.c.). This combination of FGF proteins binds to the spectrum of FGFRs. The results shown in FIG. 27 demonstrate that the particular receptor binding and signaling properties of FGF-1 are required for the observed metabolic effects.

What is claimed is:

1. A method for treating an individual having type II diabetes, comprising systemically administering an FGF-1 compound having at least 80% identity to human FGF-1 to the individual in an amount effective to reduce blood glucose levels.

2. The method of claim 1, wherein the FGF-1 compound is administered intravenously.

3. The method of claim 1, wherein the FGF-1 compound is administered subcutaneously.

4. The method of claim 1, wherein the FGF-1 compound is administered in combination with an additional therapeutic compound.

5. The method of claim 4, wherein the additional therapeutic compound is an alpha-glucosidase inhibitor, amylin agonist, dipeptidyl-peptidase 4 (DPP-4) inhibitor, meglitinide, sulfonylurea, or a peroxisome proliferator-activated receptor (PPAR)-gamma agonist.

6. The method of claim 5, wherein the PPAR agonist is a thiazolidinedione (TZD), aleglitazar, farglitazar, muraglitazar, or tesaglitazar.

7. The method of claim 6, wherein the TZD is pioglitazone, rosiglitazone, rivoglitazone, or troglitazone.

8. The method of claim 1, wherein the FGF-1 compound is a functional fragment of FGF-1 comprising at least 80% of human FGF-1.

9. The method of claim 8, wherein the functional fragment of FGF-1 comprising at least 80% of human FGF-1 comprises at least 80% sequence identity to amino acids 1-140, amino acids 1-141, amino acids 14-135, or amino acids 13-135 of FGF-1.

10. The method of claim 8, wherein the functional fragment of FGF-1 comprising at least 80% of human FGF-1 comprises amino acids 1-140, amino acids 1-141, amino acids 14-135, or amino acids 13-135 of FGF-1.

11. The method of claim 8, wherein the functional fragment of FGF-1 comprising at least 80% of human FGF-1 consists of amino acids 1-140, amino acids 1-141, amino acids 14-135, or amino acids 13-135 of FGF-1.

12. The method of claim 8, wherein the functional fragment of FGF-1 comprising at least 80% of human FGF-1 comprises at least 80% sequence identity to amino acids 14-135 of FGF1.

13. The method of claim 8, wherein the functional fragment of FGF-1 comprising at least 80% of human FGF-1 comprises amino acids 14-135 of FGF-1.

14. The method of claim 8, wherein the functional fragment of FGF-1 comprising at least 80% of human FGF-1 consists of amino acids 14-135 of FGF-1.

15. The method of claim 8, wherein the functional fragment of FGF-1 comprising at least 80% of human FGF-1 comprises at least 90% sequence identity to amino acids 1-141 of FGF-1.

16. The method of claim 8, wherein the functional fragment of FGF-1 comprising at least 80% of human FGF-1 comprises at least 95% sequence identity to amino acids 1-141 of FGF-1.

17. The method of claim 8, wherein the functional fragment of FGF-1 comprising at least 80% of human FGF-1 comprises at least 98% sequence identity to amino acids 1-141 of FGF-1.

18. The method of claim 1, wherein the FGF-1 compound is at least 90% identical to mature human FGF-1.

19. The method of claim 1, wherein the FGF-1 compound is administered daily, twice daily, every other day, bi-weekly, weekly, or monthly.

20. The method of claim 1, wherein the FGF-1 compound is a functional fragment of FGF-1 consisting of at least 90% of mature human FGF-1.

21. A method for treating an individual who is insulin resistant, comprising systemically administering an FGF-1 compound having at least 80% identity to human FGF-1 to the individual in an amount effective to reduce blood glucose levels.

22. The method of claim 21, wherein the FGF-1 compound is administered intravenously.

23. The method of claim 22, wherein the FGF-1 compound is administered subcutaneously.

24. The method of claim 21, wherein the FGF-1 compound is administered in combination with an additional therapeutic compound.

25. The method of claim 24, wherein the additional therapeutic compound is an alpha-glucosidase inhibitor, amylin agonist, dipeptidyl-peptidase 4 (DPP-4) inhibitor, meglitinide, sulfonylurea, or a peroxisome proliferator-activated receptor (PPAR)-gamma agonist.

26. The method of claim 25, wherein the PPAR agonist is a thiazolidinedione (TZD), aleglitazar, farglitazar, muraglitazar, or tesaglitazar.

27. The method of claim 26, wherein the TZD is pioglitazone, rosiglitazone, rivoglitazone, or troglitazone.

28. The method of claim 21, wherein the FGF-1 compound is a functional fragment of FGF-1 comprising at least 80% of human FGF-1.

29. The method of claim 28, wherein the functional fragment of FGF-1 comprising at least 80% of human FGF-1 comprises at least 80% sequence identity to amino acids 1-140, amino acids 1-141, amino acids 14-135, or amino acids 13-135 of FGF1.

30. The method of claim 28, wherein the functional fragment of FGF-1 comprising at least 80% of human FGF-1 comprises amino acids 1-140, amino acids 1-141, amino acids 14-135, or amino acids 13-135 of FGF-1.

31. The method of claim 28, wherein the functional fragment of FGF-1 comprising at least 80% of human FGF-1 consists of amino acids 1-140, amino acids 1-141, amino acids 14-135, or amino acids 13-135 of FGF-1.

32. The method of claim 28, wherein the functional fragment of FGF-1 comprising at least 80% of human FGF-1 comprises at least 80% sequence identity to amino acids 14-135 of FGF-1.

33. The method of claim 28, wherein the functional fragment of FGF-1 comprising at least 80% of human FGF-1 comprises amino acids 14-135 of FGF-1.

34. The method of claim 28, wherein the functional fragment of FGF-1 comprising at least 80% of human FGF-1 consists of amino acids 14-135 of FGF-1.

35. The method of claim 21, wherein the FGF-1 compound is at least 90% identical to mature human FGF-1.

36. The method of claim 28, wherein the functional fragment of FGF-1 comprising at least 80% of human FGF-1 comprises at least 90% sequence identity to amino acids 1-141 of FGF-1.

37. The method of claim 28, wherein the functional fragment of FGF-1 comprising at least 80% of human FGF-1 comprises at least 95% sequence identity to amino acids 1-141 of FGF-1.

38. The method of claim 28, wherein the functional fragment of FGF-1 comprising at least 80% of human FGF-1 comprises at least 98% sequence identity to amino acids 1-141 of FGF-1.

39. The method of claim 1, wherein the FGF-1 compound is administered daily, twice daily, every other day, bi-weekly, weekly, or monthly.

40. The method of claim 1, wherein the FGF-1 compound is a functional fragment of FGF-1 consisting of at least 90% of mature human FGF-1.

* * * * *

UNITED STATES PATENT AND TRADEMARK OFFICE
CERTIFICATE OF CORRECTION

PATENT NO. : 8,906,854 B2
APPLICATION NO. : 14/184621
DATED : December 9, 2014
INVENTOR(S) : Jonker et al.

It is certified that error appears in the above-identified patent and that said Letters Patent is hereby corrected as shown below:

In the Abstract:
On line 3 of the Abstract, "dyslipidaemia" should be --dyslipidemia--.

In the Specification:
Column 5, line 44, "hepatocyes" should be --hepatocytes--.
Column 5, line 64, "subcutaenous" should be --subcutaneous--.
Column 12, line 3, "acitivities" should be --activities--.
Column 12, line 26, "155 amino acid human sequence" should be --140 amino acid human sequence (or mature FGF-1)--.
Column 12, line 56, "carboxy" should be --carboxyl--.
Column 12, line 61, "polysialyic" should be --polysialic--.
Column 16, line 11, "dyslipidaemia" should be --dyslipidemia--.
Column 17, line 67 – column 18, line 1, "intravesicularlly" should be --intravesicularly--.
Column 18, line 4, "creme" should be --cream--.

Signed and Sealed this
Sixteenth Day of February, 2016

Michelle K. Lee
*Director of the United States Patent and Trademark Office*